US006991713B2

(12) United States Patent
Adourian et al.

(10) Patent No.: US 6,991,713 B2
(45) Date of Patent: Jan. 31, 2006

(54) METHODS AND APPARATUS FOR PROCESSING A SAMPLE OF BIOMOLECULAR ANALYTE USING A MICROFABRICATED DEVICE

(75) Inventors: Aram S. Adourian, Watertown, MA (US); Daniel J. Ehrlich, Lexington, MA (US); Lance B. Koutny, Methuen, MA (US); Paul T. Matsudaira, Wayland, MA (US); Dieter R. Schmalzing, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 1004 days.

(21) Appl. No.: 09/768,075

(22) Filed: Jan. 23, 2001

(65) Prior Publication Data

US 2001/0020588 A1    Sep. 13, 2001

Related U.S. Application Data

(62) Division of application No. 09/153,215, filed on Sep. 14, 1998, now Pat. No. 6,207,031.

(60) Provisional application No. 60/058,798, filed on Sep. 15, 1997.

(51) Int. Cl.
*G01N 27/26*    (2006.01)
*G01N 27/447*    (2006.01)
(52) U.S. Cl. .................. 204/453; 204/451; 204/455; 204/601; 204/604; 204/605; 422/100
(58) Field of Classification Search ........ 204/450–455, 204/600–605; 422/100; 436/514–516; 435/4–40.52
See application file for complete search history.

(56) References Cited

U.S. PATENT DOCUMENTS 4,292,920 A * 10/1981 Smith et al. ................. 118/425

(Continued)

FOREIGN PATENT DOCUMENTS

WO    WO96/35810    11/1996

OTHER PUBLICATIONS

A. Manz et al, "Electroosmotic pumping and electrophoretic separations for miniaturized chemical analysis systems." J. Micromech. Microeng. 4 (1994) 257-265.*

(Continued)

*Primary Examiner*—Nam Nguyen
*Assistant Examiner*—Jeffrey Barton
(74) *Attorney, Agent, or Firm*—Hamilton, Brook, Smith & Reynolds, P.C.

(57) ABSTRACT

A technique processes a sample of biomolecular analyte. The technique uses an apparatus having a support assembly that receives and supports a test module, a load assembly that loads the sample of biomolecular analyte onto the test module, an electrophoresis assembly that applies a current to the test module such that components within the sample separate by electrophoresis, and a controller that controls operations of the load assembly and the electrophoresis assembly. The load assembly and the electrophoresis assembly are coupled to the support assembly. The controller controls the operation of the load assembly in an automated manner. Preferably, the test module includes a dielectric plate member having an upper planar surface and a lower planar surface that is spaced apart from and coplanar with the upper planar surface. The dielectric plate member has at least one set of channels that includes an injection channel and a separation channel. The injection channel extends from the upper planar surface to the lower planar surface. The separation channel extends within the dielectric plate member in a plane parallel with the upper and lower planar surfaces and intersects the injection channel.

20 Claims, 14 Drawing Sheets

U.S. PATENT DOCUMENTS

| | | | | |
|---|---|---|---|---|
| 4,495,149 | A | | 1/1985 | Iwata et al. .................... 422/65 |
| 4,827,780 | A | | 5/1989 | Sarrine et al. ............ 73/864.21 |
| 4,908,112 | A | | 3/1990 | Pace .......................... 204/299 |
| 4,954,237 | A | | 9/1990 | Sarrine et al. .............. 204/299 |
| 5,202,010 | A | * | 4/1993 | Guzman ..................... 204/601 |
| 5,437,838 | A | | 8/1995 | DeMoranville et al. ....... 422/67 |
| 5,455,008 | A | * | 10/1995 | Earley et al. ............... 422/100 |
| 5,560,811 | A | | 10/1996 | Briggs et al. ............... 204/451 |
| 5,571,410 | A | * | 11/1996 | Swedberg et al. ....... 210/198.2 |
| 5,585,069 | A | * | 12/1996 | Zanzucchi et al. .......... 422/100 |
| 5,630,924 | A | * | 5/1997 | Fuchs et al. ................ 204/601 |
| 5,770,029 | A | * | 6/1998 | Nelson et al. ............. 204/604 |
| 5,824,204 | A | * | 10/1998 | Jerman ....................... 204/601 |
| 5,851,370 | A | | 12/1998 | Maracas et al. ............ 204/450 |
| 5,872,010 | A | * | 2/1999 | Karger et al. ............... 436/173 |
| 5,876,675 | A | * | 3/1999 | Kennedy ..................... 422/99 |
| 5,993,634 | A | * | 11/1999 | Simpson et al. ............ 204/612 |
| 6,086,825 | A | * | 7/2000 | Sundberg et al. ........... 422/100 |

OTHER PUBLICATIONS

Schmalzing, Dieter, et al., "DNA Typing in thirty seconds with a microfabricated device," *Proc. Natl. Acad. Sci. USA,* 94: 10273.-10278, Sep. 1997.

Woolley, Adam T., et al., High-Speed DNA Genotyping Using Microfabricated Capillary Array Electrophoresis Chips, *Anal. Chem,.* 69:2181-2186, 1997.

Woolley, A. T., and Mathies, R. A., "Ultra-High-Speed DNA Sequencing Using Capillary Electrophoresis Chips," *Anal. Chem.,* 67:3676-3680, 1995.

Woolley, A.T., and Mathies, R.A., "Ultra-high-speed DNA fragment separations using microfabricated capillary array electrophoresis chips," *Proc. Natl. Acad. Sci. USA,* 91: 11348-11352, Nov. 1994.

Fan, Zhonghui H., and Harrison, D. Jed, "Micromachining of Capillary Electrophoresis Injectors and Separators on Glass Chips and Evaluation of Flow at Capillary Intersections," *Anal. Chem.,* 66:177-184, 1994.

Harrison, D. Jed, et al., "Capillary Electrophoresis and Sample Injection Systems Integrated on a Planar Glass Chip," *Anal. Chem.,* 64:1926-1932, 1992.

Wang, Y., et al., "Rapid Sizing of Short Tandem Repeat Alleles Using Capillary Array Electrophoresis and Energy-Transfer Fluorescent Primers," *Analytical Chemistry, 67(7):* 1197-1203 (Apr. 1, 1995).

* cited by examiner

METHODS AND APPARATUS FOR PROCESSING A SAMPLE OF BIOMOLECULAR ANALYTE USING A MICROFABRICATED DEVICE

RELATED APPLICATIONS

This application is a divisional of application Ser. No. 09/153,215, filed Sep. 14, 1998, now U.S. Pat. No. 6,207, 031,which claims the benefit of U.S. Provisional Application No. 60/058,798, filed on Sep. 15, 1997.

The entire teachings of the above application(s) are incorporated herein by reference.

GOVERNMENT SUPPORT

The invention was supported, in whole or in part, by Grant No. RO1 HG01389 from the National Institutes of Health and Grant No. F49620-95-1-0165 from the Defense Advanced Research Projects Agency/Air Force Office of Scientific Research. The Government has certain rights in the invention.

BACKGROUND OF THE INVENTION

The human genome includes stretches of DNA composed of short tandem repeats (STRs). The analysis of such STRs is an important tool for genetic linkage studies, forensics, and new clinical diagnostics because STRs are abundant and their locations have been mapped in genomes.

A typical STR is less than 400 base pairs in length, and includes repetitive units that are two to seven base pairs in length. STRs can define alleles which are highly polymorphic due to large variations between individuals in the number of repeats. For example, four loci in the human genome CSF1PO, TPOX, THO1, and vWA (abbreviated CTTv) are characterized by an STR allele which differs in the number of repeats. Two repeating units are found at these loci: AATG for TPOX and THO1, and AGAT for CSF1PO and vWA.

In general, STR analysis involves generating an STR profile from a DNA sample, and comparing the generated STR profile with other STR profiles. Generating an STR profile typically involves dying or tagging STRs within a DNA sample, separating the tagged STRs within the sample using electrophoresis (applying an electric field), and recording the tagged STRs using a detector (e.g., a laser and a scanner).

One procedure for generating an STR profile uses an elongated gel plate (or slab gel) that is approximately 35 cm long. In general, this process (hereinafter referred to as "the gel plate process") involves depositing a tagged DNA sample on an area of the gel plate, separating the STRs within the tagged DNA sample on the gel plate using electrophoresis, and scanning the gel plate with a detector to record the tagged STRs. Typically, the gel plate process requires two to three hours to complete.

Another procedure for generating an STR profile uses a capillary that is 50 to 75 microns in diameter. This process (hereinafter referred to as "the capillary process") generally involves placing a tagged DNA sample at one end of a capillary, and drawing the sample through the capillary using electrophoresis to separate the STRs. A detector records the STRs by scanning a portion of the capillary.

Typically, STR separation is faster in the capillary process than in the gel plate process. In general, an increase in electrophoresis current results in an increase in STR separation speed, and a higher electrophoresis current typically can be applied to the capillary than to the gel plate because the capillary more easily dissipates heat (caused by the current) which would otherwise skew the separation results. A typical capillary process requires between 10 minutes and one hour to complete.

Another procedure for generating an STR profile uses a microchip (or chip) made of durable transparent glass or plastic. A typical microchip is a monolithic structure that is planar in shape. Such a microchip includes multiple pairs of channels (channel pairs) that run in a coplanar manner with the plane of the microchip. An individual STR separation can be performed at each channel pair. Each channel pair includes a long channel and a short channel. The short channel intersects the long channel near one end of the long channel and at a 90 degree angle. In some microchips, the short channel includes a jog where it intersects the long channel such that portions of the short channel are parallel but not co-linear. Typically, a microchip is formed using photolithography and chemical etching techniques to produce channel structures in fused silica wafers.

An STR separation process that uses a microchip (hereinafter referred to as "the microchip process") generally involves orienting the microchip so that it and the channels within lie horizontally (i.e., perpendicular to the direction of gravity) and depositing a sample of tagged DNA over a hole in the upper surface of the microchip that connects with one end of the short channel of a channel pair. Next, the DNA sample is drawn horizontally through the short channel using electrophoresis such that STRs within the sample are partially separated along the short channel. Then, a portion of the sample at the intersection of the long and short channels is further separated along the long channel using electrophoresis. A detector records the STRs in a manner similar to that of the gel plate and capillary processes.

The microchip process provides advantages over the gel plate and capillary processes. First, the microchip process requires less time to complete than the gel plate and capillary processes because, in the microchip process, very large STRs (which impede STR separation in the gel plate and capillary processes) are removed from the DNA sample during electrophoresis along the short channel and thus do not impede STR separation along the long channel. Accordingly, STR separation along the long channel takes no more than a few minutes. Second, a microchip may include multiple channel pairs such that multiple samples can be separated and scanned simultaneously. Nevertheless, significant decreases in electrophoretic run-times would greatly increase the speed of STR analysis.

Conventional high-speed DNA genotyping using a microchip is described in an article entitled "High-Speed DNA Genotyping Using Microfabricated Capillary Array Electrophoresis Chips", Analytical Chemistry, Vol. 69, No. 11, Jun. 1, 1997 on pages 2181 through 2186, the teachings of which are hereby incorporated by reference in their entirety. Ultra-high-speed DNA sequencing using capillary electrophoresis chips is described in an article entitled "Ultra-High-Speed DNA Sequencing Using Capillary Electrophoresis Chips", Analytical Chemistry, Vol. 67, No. 20, Oct, 15, 1995 on pages 3676 through 3680, the teachings of which are hereby incorporated by reference in their entirety.

SUMMARY OF THE INVENTION

In general, the term "biomolecular analyte" refers to both non-synthetic and synthetic nucleic acids (e.g., DNA and RNA) and portions thereof, and biological proteins.

Described herein are practical ultra-fast techniques for allelic profiling of such biomolecular analyte. In particular, the techniques involve using a microfluidic electrophoresis device to analyze short tandem repeats (STRs) within a DNA sample. An assay method of the present invention has made it possible to rapidly achieve baseline-resolved electrophoretic separations of single-locus STR samples. In one embodiment, the assay permits baseline-resolved electrophoretic separations of single-locus STR samples in approximately 30 seconds. In addition, analysis of samples (e.g., PCR samples) containing loci defined or characterized by an STR which differs in the number or repeats is performed rapidly (e.g., at a rate which represents a 10-to-100-fold improvement in speed relative to capillary or slab gel systems) using the allelic profiling assay described herein. For example, analyses of PCR samples containing the four loci CSF1PO, TPOX, THO1 and vWA (abbreviated as CTTv) can be performed in less than two minutes. This constitutes a 10-to-100-fold improvement in speed relative to capillary or slab gel systems.

Also described herein is a separation device (or test module) useful in an allelic profiling assay of the present invention. The separation device includes a microfabricated channel device having a channel of sufficient dimensions in cross-section and length to permit a sample to be analyzed rapidly. In one embodiment, the separation device consists of a microfabricated channel 45 μm×100 μm in cross-section and 26 mm in length, that is filled with a replaceable polyacrylamide matrix operated under denaturing conditions at 50° C. A fluorescently labeled STR ladder is used as an internal standard for allele identification. Samples analyzed by the assay method can be prepared by standard procedures and only small volumes (e.g., 4 μL) are required per analysis. The device is capable of repetitive operation and is suitable for automated high-speed and high-throughput applications.

The term "test plate" is used hereinafter to refer to a dielectric structure having an intersecting channel pair structure. Other terms that are interchangeable with the term test plate are microfabricated channel device, microchip, chip, electrophoresis chip and ME device.

An embodiment of the invention is directed to an apparatus for processing a sample of biomolecular analyte. The apparatus includes a support assembly that receives and supports a test module, a load assembly that loads the sample of biomolecular analyte on the test module, an electrophoresis assembly that applies a current to the test module such that components within the sample separate by electrophoresis, and a controller that controls operations of the load and electrophoresis assemblies. The load assembly and the electrophoresis assembly are coupled to the support assembly. The controller controls the operation of the load assembly in an automated manner.

The sample of biomolecular analyte may be disposed about a bead that is magnetically attractable. To this end, the load assembly may include an electromagnetic loading device that, in response to the controller, (i) electromagnetically carries the bead from a sample source to the test module using electromagnetism, and (ii) releases the bead into the test module. The load assembly may further include an electromagnetic unloading device that provides a force on the bead in a direction toward the test module and away from the electromagnetic loading device in response to the controller. The bead can be constructed such that it releases the sample of biomolecular analyte when deposited in the test assembly.

Alternatively, the apparatus may include a capillary that, in response to the controller, (i) transfers the sample from a sample source to the test module using electrokinetics, and (ii) terminates transfer of the sample. The load assembly may further include a gasket that forms a hermetic seal between the capillary and the test module when the capillary transfers the sample from the sample source to the test module. In this situation, it is unnecessary to contain the biomolecular analyte in a magnetically attractable bead.

Preferably, the apparatus further includes a detection assembly, coupled to the support assembly, that detects the components within the sample. The detection assembly may include an actuating member, coupled to the support assembly, and a scanner, coupled to the actuating member. The scanner scans the test module. The actuating member moves the scanner, in response to the controller, between (i) a first position adjacent the support assembly that receives and supports the test module and (ii) a second position adjacent the support assembly that receives and supports another test module.

The apparatus may further include an injection assembly, coupled to the support assembly, that injects fluid into the test module to facilitate separation of the components within the sample by electrophoresis. Accordingly, the injection assembly can preload the test module with a matrix in an automated manner prior to loading the test module with the sample of biomolecular analyte.

The apparatus may further include a set of electrical connections that provides power from a power supply to the test module. Accordingly, if the test module includes electrical circuitry (e.g., a heating device for providing heat to the sample), the test module can obtain power for the circuitry from the apparatus.

The load assembly may further include a robotic device, coupled to the support assembly, having an arm and an actuator that moves the arm between a sample source and the test module. Additionally, the load assembly may include a load device, coupled to the arm of the robotic device, that transfers the sample of biomolecular analyte from the sample source to the test module. Furthermore, the load assembly may include a camera, coupled to the arm of the robotic device, that determines a position of the arm of the robotic device and indicates the position to the controller. The controller moves the arm of the robotic device according to the indicated position.

The support assembly of the apparatus may include a support member that supports multiple test modules. Furthermore, the apparatus may include a detector that moves relative to the support member to scan each of the multiple test modules supported by the support member. Alternatively, the support member may move the multiple test modules relative to the detector such that the detector scans each test module.

Another embodiment is directed to a method for loading a test plate with a sample of biomolecular analyte that is disposed about a bead that is magnetically attractable. The method includes the steps of activating an electromagnetic loading device to attract and carry the bead, and positioning the electromagnetic loading device adjacent an opening of the test plate. The method further includes the step of deactivating the electromagnetic loading device to release the bead at the opening of the test plate such that the sample of biomolecular analyte is loaded on the test plate.

The method may further include the step of activating an electromagnetic unloading device that provides a force on the bead in a direction away from the electromagnetic loading device and toward the opening of the test plate.

Accordingly, any bead material remaining on the electromagnetic loading device after the electromagnetic loading device is deactivated will be attracted away from the electromagnetic loading device and toward the test plate.

Preferably, the step of positioning the electromagnetic loading device includes the step of actuating a robotic assembly that supports the electromagnetic loading device such that the electromagnetic loading device moves to a programmed position relative to the test plate. This allows the sample to be positioned accurately and consistently from test to test.

Another embodiment of the invention is directed to a method for loading a test plate with a sample of biomolecular analyte that is disposed within a solution. The method includes the steps of positioning a capillary adjacent an opening of the test plate, and activating an electrokinetics device coupled to a capillary such that the sample is drawn through the capillary onto the test plate by electrokinetics. The method further includes the step of deactivating the electrokinetics device such that the sample is no longer drawn through the capillary. The step of activating preferably includes the step of dispensing a fluid droplet of the sample onto the test plate.

Another embodiment of the invention is directed to a test module assembly. The test module assembly includes a dielectric plate member having an upper planar surface and a lower planar surface that is spaced apart from and coplanar with the upper planar surface. The dielectric plate member has at least one set of channels that includes an injection channel and a separation channel. The injection channel extends from the upper planar surface to the lower planar surface. The separation channel extends within the dielectric plate member in a plane parallel with the upper and lower planar surfaces and intersects the injection channel. Preferably, the injection channel intersects the separation channel at a right angle, and terminates at the upper and lower planar surfaces at right angles to the upper and lower planar surfaces. The plate member is preferably wedge shaped.

The test module assembly may further include a housing that attaches to the dielectric plate member. The housing provides (i) a first opening over the upper planar surface such that a first end of the injection channel is accessible through the first opening, and a second opening over the lower planar surface such that a second (i.e., opposite) end of the injection channel is accessible through the second opening. The housing may further provide a third opening over either the upper planar surface or the lower planar surface such that the separation channel is accessible to a detection device through the third opening.

Preferably, the test module assembly includes a heating device, supported by the housing, that provides heat to the dielectric plate member when power is provided to the heating device. The heat facilitates the separation of components within the sample during electrophoresis.

The test module assembly may further include a first porous membrane that covers the first end of the injection channel and a second porous membrane that covers the second end of the injection channel to retain a matrix within the injection and separation channels. The first and second porous membranes may be adhered to the dielectric plate member.

The test module assembly may further include an electromagnetic unloading device, supported by the housing, that draws magnetic material for testing towards the dielectric plate member when the electromagnetic unloading device is activated. Accordingly, a sample of biomolecular analyte that is about a magnetically attractable bead will be drawn away toward the dielectric plate member when unloading the sample.

Preferably, the dielectric plate member includes multiple sets of channels. Each set of channels includes an injection channel and a separation channel. The injection channel of each set extends from the upper planar surface to the lower planar surface. The separation channel of each set extends within the dielectric plate member in a plane parallel with the upper and lower planar surfaces and intersects the injection channel of that set. The injection channels of the multiple sets of channels may be parallel with each other. These features of the invention increase the channel density (i.e., the number of channel sets per unit area of the plate member) of the dielectric plate member enabling more tests to be scanned by an individual scanner in a fixed position relative to the dielectric plate member. Furthermore, the orthogonal orientation of the injection channels (relative to the plane of the plate member) improves initial separation of the components within the sample during electrophoresis in the direction of the injection channel.

Another embodiment of the invention is directed to a method for separating a sample of biomolecular analyte. The method includes the step of drawing the sample along a longitudinal axis of an injection channel of a test plate using electrokinetics. The test plate is planar in shape along an orthogonal axis to the longitudinal axis of the injection channel. The method further includes the step of subsequently drawing the sample along the orthogonal axis through a separation channel of the test plate using electrokinetics. The separation channel intersects the injection channel within the test plate.

The method may further include the steps of drawing multiple samples along the longitudinal axes of multiple other injection channels using electrokinetics simultaneously with the step of drawing the sample, and drawing the multiple samples along other orthogonal axes through multiple other separation channels using electrokinetics. The multiple other separation channels respectively intersect the multiple other injection channels.

Preferably, the method further includes the step of scanning a respective portion of the separation channel and the multiple other separation channels with a detection device.

Another embodiment of the invention is directed to a system for analyzing short tandem repeats within a sample of biomolecular analyte. The system includes a test plate having a separation channel, a support assembly that supports the test plate, an automated loading device that loads the sample of biomolecular analyte on the test plate in an automated manner, and an electrophoresis device that separates short tandem repeats in the sample within the separation channel of the test plate. The automated loading device and the electrophoresis device are coupled to the support assembly.

Preferably, the automated loading device includes a robotic actuator assembly, coupled to the support assembly, that obtains the sample from a sample source and deposits the sample at a particular location on the test plate.

Alternatively, the automated loading device includes a capillary assembly, coupled to the support assembly, that obtains the sample from a sample source (e.g., using electrokinetics) and deposits the sample at a particular location on the test plate.

The system may further include a detection device that detects the short tandem repeats within the separation channel of the test plate.

Another embodiment of the invention is directed to method for analyzing short tandem repeats within a sample of biomolecular analyte. The method includes the steps of providing a test plate having a separation channel, activating an automated loading device that loads the sample of biomolecular analyte on the test plate in an automated manner, and connecting an electrophoresis device to the test plate and activating the electrophoresis device to separate short tandem repeats in the sample within the separation channel of the test plate.

Another embodiment of the invention is directed to a test module assembly that includes a rotatable dielectric plate member having an upper planar surface and a lower planar surface that is spaced apart from and coplanar with the upper planar surface. The rotatable dielectric plate member has multiple separation channels that extend within the dielectric plate member in a plane parallel with the upper and lower planar surfaces. The multiple separation channels extend radially from an inner portion of the dielectric plate member to an outer portion of the dielectric plate member.

Preferably, the rotary dielectric plate member is disk shaped and further includes multiple injection channels. Each injection channel may intersect a corresponding separation channel within the outer portion of the dielectric plate member.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

There is a compelling need for improved throughput and reduced cost for electrophoretic separation of biologically important molecules, especially for such applications as DNA sequencing and DNA typing. Traditional aspects of the supporting technology including traditional pipette loading and labor-intensive preparation of gel plates have constrained attempts to miniaturize the apparatus and to increase parallelism.

Figure 1:
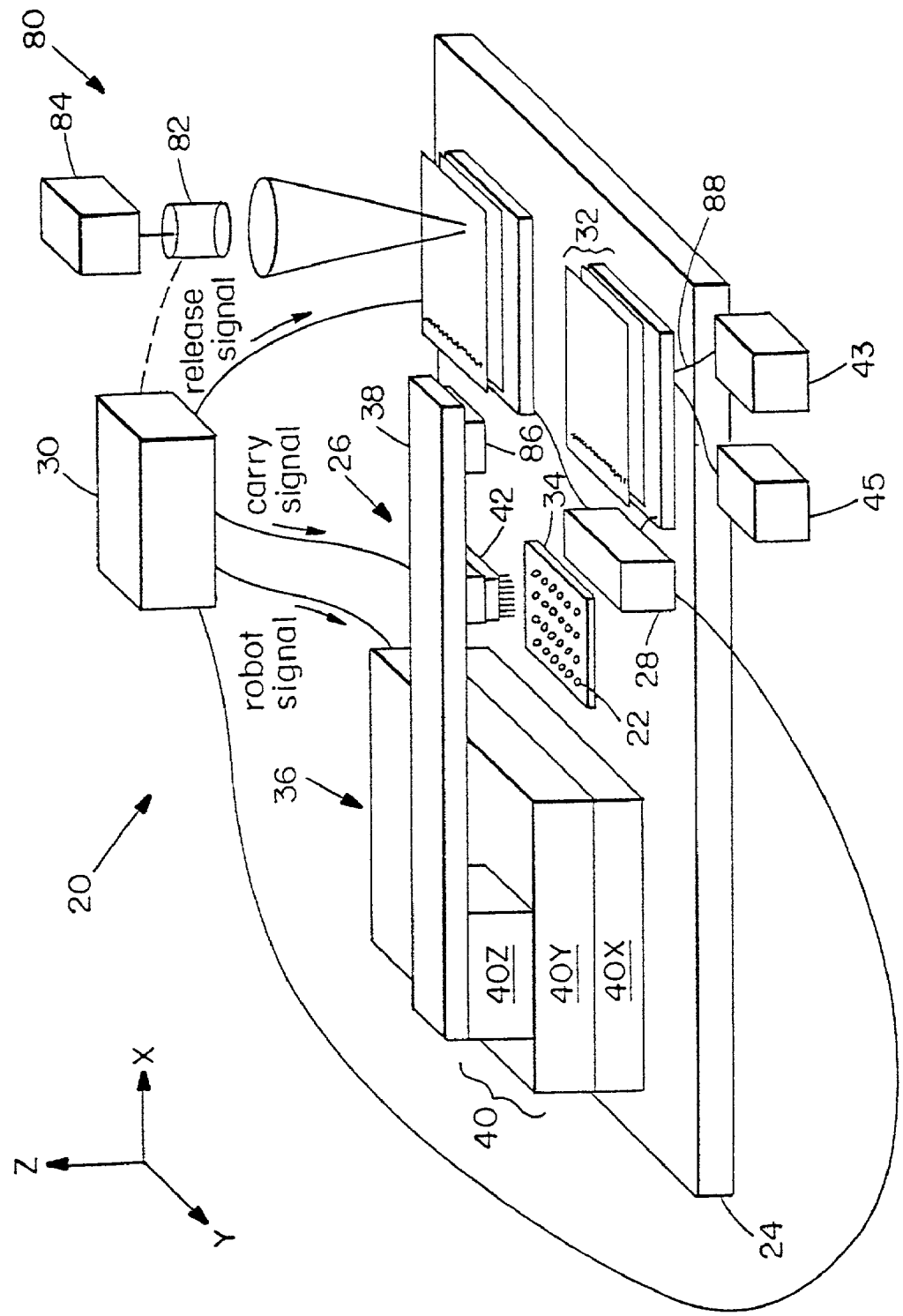
FIG. 1 is a perspective view of a system for processing biomolecular analyte according to the invention.

In contrast to conventional techniques, an embodiment of the invention is directed to an automated technique for processing a sample of biomolecular analyte with improved throughput and reduced preparation requirements. The embodiment involves the use of an apparatus 20 for processing a sample 22 of biomolecular analyte, as shown in FIG. 1. The apparatus 20 includes a support assembly 24, a load assembly 26, an electrophoresis assembly 28, and a controller 30. The support assembly 24 receives and supports a test module 32 including multiple channel pairs (channel sets for testing respective samples). The load assembly 26 obtains one or more samples 22 from a sample source 34, and loads the samples 22 simultaneously (in parallel) into respective channels/ports on the test module 32. The electrophoresis assembly 28 applies a current to the test module 32 such that components within the samples 22 (e.g., STRs) separate by electrophoresis. The controller 30 controls the operations of the load and electrophoresis assemblies 26, 28.

The load assembly 26 includes a robotic device 36 having a robotic arm 38 and an actuation assembly 40. The load assembly 26 further includes a fluid transfer device 42 that is attached to the robotic arm 38. The fluid transfer device 42 has an array of electrically conductive fluid (sample) dispensing tips that carry sample material from the sample source 34 to respective injection channels in the test module 32. The actuation assembly 40 moves the robotic arm 38 and the fluid transfer device 42 according to a robot signal provided by the controller 30. In particular, the actuation assembly 40 includes actuators 40X, 40Y and 40Z that are capable of moving the robotic arm 38 and the fluid transfer device 42 along the X-axis, Y-axis and Z-axis, respectively. Preferably, the robotic device 36 provides both linear motion (along any combination of the X, Y and Z axes) and rotary motion (about the axes).

Figure 2:
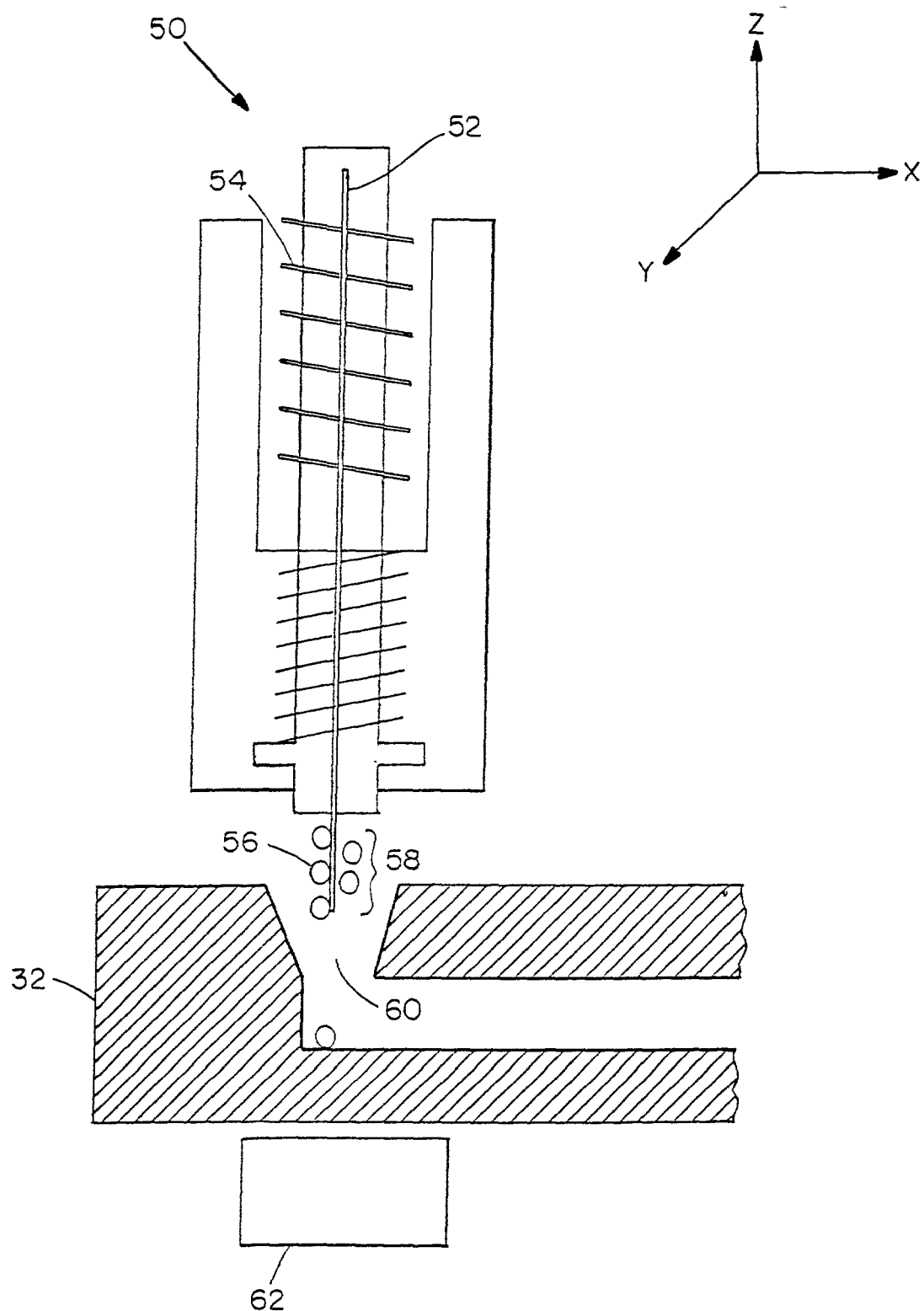
FIG. 2 is a side view of a load assembly and test module of the system of FIG. 1.

During operation, the fluid transfer device 42 interfaces with both the sample source 34 (e.g., a microtitre plate) and the test module 32 (e.g., a microchip assembly). Preferably, each dispensing tip in the array of dispensing tips of the fluid transfer device 42 includes an electromagnetic loading device 50 having a core 52 and windings 54, as shown in FIG. 2. The controller 30 activates the electromagnetic device 50 by providing a carry signal to the windings 54. The sample 22 of biomolecular analyte preferably is disposed about magnetically attractable beads 56. The controller 30 positions the fluid transfer device 50 over the sample source 34 and activates the electromagnetic device 50. In turn the core 52 becomes magnetically charged such that a distal or working end 58 of the core 52 attracts, picks up and retains the beads 56. Then, the controller 30 operates the robotic device 36 to move the fluid transfer device 42 over the test module 32 such that the distal end 58 of the core 52 is adjacent a target opening 60 (injection port) of the test module 32, as shown in FIG. 2. Next, the controller 30 discontinues providing the carry signal to deactivate the electromagnetic loading device 50. Accordingly, the core 52 becomes demagnetized and the beads 56 are released from the end 58 of the core 52 and drop into the target opening 60 of the test module 32.

As will be discussed later in further detail, the test module 32 includes a microchip that contains an internal sieving matrix and a microfabricated coverplate. The test module 32 may be driven with a high voltage supply 43 and a temperature controller 45 (see FIG. 1).

The load assembly 26 may further include an electromagnetic unloading device 62, as shown in FIG. 2. The electromagnetic unloading device 62 is positioned beneath the target opening 60 such that the target opening 60 of the test module 32 is between the electromagnetic loading device 50 and the electromagnetic unloading device 62. When the controller 30 discontinues providing the carry signal to deactivate the electromagnetic loading device 50, the controller 30 simultaneously provides a release signal to the electromagnetic unloading device 62 to draw the beads away from the end 58 of the core 52 and toward the target opening 60 of the test module 32. Accordingly, the electromagnetic unloading device 62 provides a magnetic force on any beads that may have otherwise stuck to the end 58 of the core 52 to unload them into the target opening 60.

Figure 3:
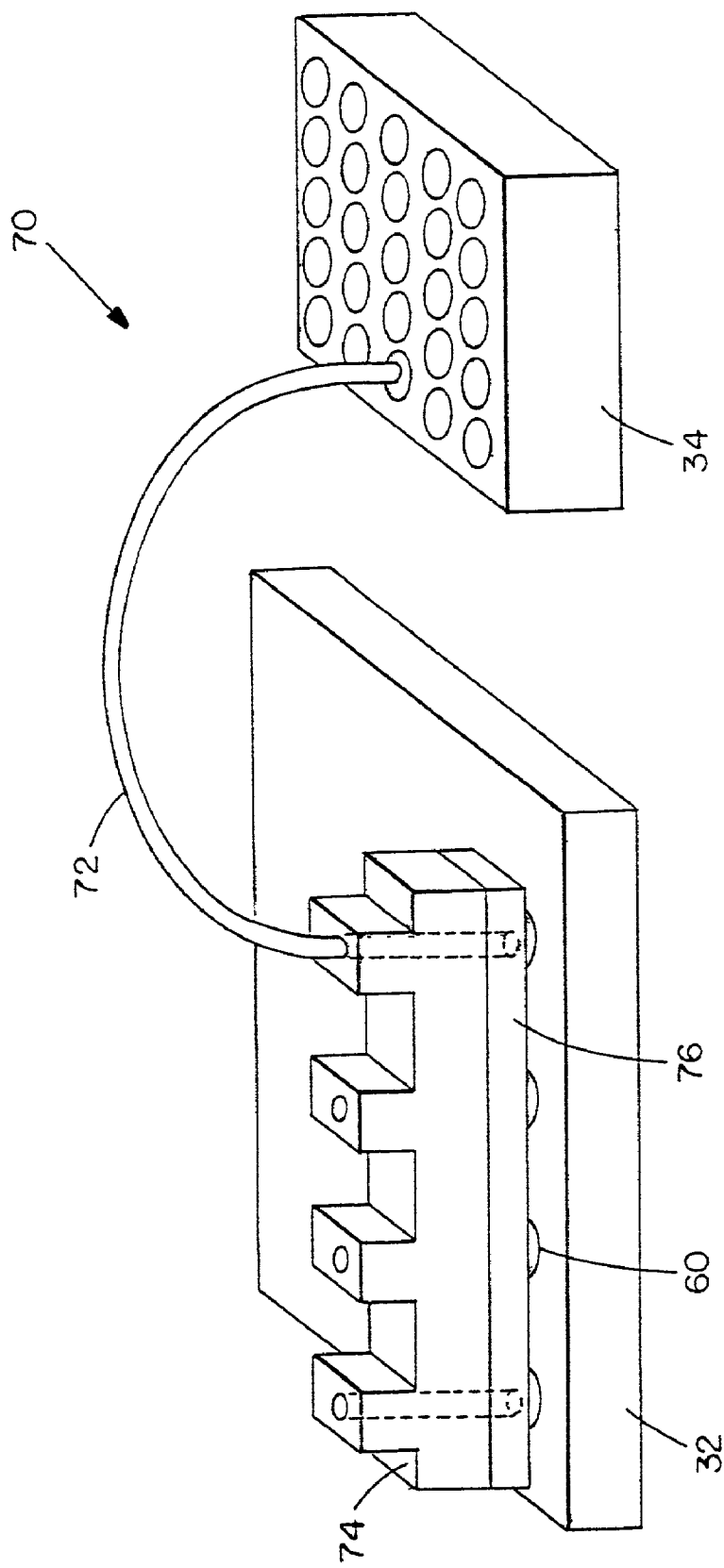
FIG. 3 is a perspective view of an alternative load assembly for the system of FIG. 1.

As an alternative to the robotic device 36 (see FIG. 1) and the electromagnetic devices 50, 62 (see FIG. 2), the load assembly 26 may include a capillary assembly 70, as shown in FIG. 3. The capillary assembly 70 includes multiple capillaries 72 (one shown), a rigid support 74 and a non-rigid gasket 76. When the rigid support 74 is positioned properly over the test module 32, the gasket 76 forms a hermetic, liquid-tight seal with the test module 32 to prevent contamination. The rigid support 74 positions the proximal ends of the capillaries 72 such that they match with corresponding target openings 60 of the test module 32. In particular, the rigid support 74 provides appropriately sized and spaced holes and structural support to maintain the proximal ends of the capillaries rigidly in place. Preferably, the capillaries are made of glass and the proximal ends of the capillaries extend through the rigid support 74 and at least a portion of the non-rigid gasket 76. The other (opposite) ends of the capillaries 72 mate with the sample source 34 in a conventional manner. In particular, the other ends of the capillaries 72 connect with wells of a microtitre plate of the sample source 34.

For the capillary assembly of FIG. 3, the sample source 34 includes samples of biomolecular analyte in fluid form. The capillary assembly 70 injects the samples into the test module 32 by transferring the samples from the source to the test module 32 electrokinetically. That is, the load assembly 26 provides a voltage between the sample source 34 (e.g., microtitre plate wells) and the test module 32 (e.g., microfluidic channels within a microchip) such that the samples migrate from the sample source 34 to the test module 32.

Preferably, each capillary dispenses a sample fluid droplet onto the test module 32. Such a droplet may be released by a physical pulse (e.g., from a pulse device). An advantage of such a system is the ability to load multiple samples simultaneously through multiple capillaries onto the test module 32 and into multiple injection channels therein.

Reference is made back to FIG. 1 for a further discussion of the apparatus 20. After the test module 32 has been loaded with one or more samples 22 from the sample source 34, the electrophoresis assembly 28 applies an electrical current to the test module 32 to separate the components (e.g., STRs) within each sample 22. The apparatus 20 preferably includes a detection assembly 80 which then detects these separated components. The detection assembly 80 includes a scanner 82 and an actuator 84 that moves the scanner 82 to various scanning positions relative to the support assembly 24. In particular, the actuator 84 moves the scanner 82 to a pertinent portion of each channel set of the test module 32 to detect respective separation components. The detection assembly 80 collects data from the test module 32 and provides the data electronically to a data storage system of the controller 30.

Preferably, the support assembly 24 is capable of receiving and supporting multiple test modules 32, as shown in FIG. 1. In this situation, the actuator 84 of the detection assembly preferably moves the scanner 82 between multiple positions over the multiple test modules 32 (e.g., between a first position adjacent a first test module and a second position over a second test module as well as multiple locations within each of the first and second positions for detecting respective multiple channels and the separated components therein).

Preferably, the apparatus 20 further includes an injection assembly 86 that injects fluid (e.g., a separation matrix) into each test module 32 prior to sample loading. The fluid facilitates separation of the sample components during electrophoresis. Such automated loading enables injection of ultrathin gels (eliminating manual pouring of gels) and permits the use of unbonded microchips (greatly reducing the cost and increasing the re-usability of the microchips).

The apparatus 20 may further include power supply connections 88 that provide power to each test module 32 from the voltage supply 43. Accordingly, circuitry within each test module 32 (e.g., a heater) can be powered to facilitate component separation during electrophoresis.

It should be understood that the apparatus 20 provides sample loading, sample separation and sample detection of one or more samples in parallel, in an automated manner. That is, such operations can be performed without human intervention. As such, the robotic loading of the sample 22 is easily repeatable and requires minimal preparation. In particular, the controller 30 stores programmed positions enabling the fluid transfer device 42 of the load assembly 26 to automatically transfer samples 22 from the sample source 34 to respective ports/channels of each test module 32 for testing. Accordingly, labor-intensive sample loading, which is common with conventional techniques, is unnecessary when using the apparatus 20.

Figure 4:
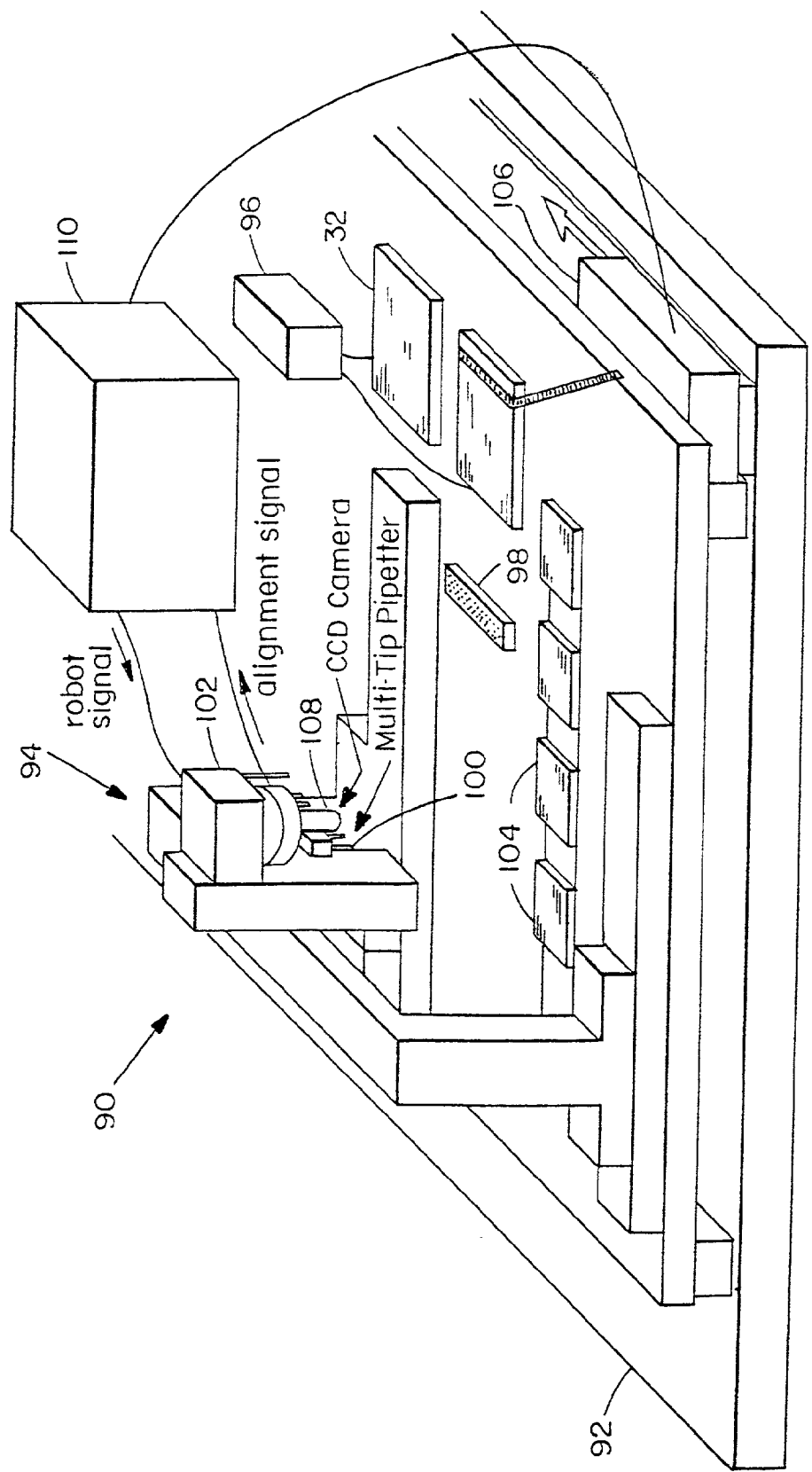
FIG. 4 is a perspective view of another system for processing biomolecular analyte according to the invention.

Another apparatus 90 for processing a sample of biomolecular analyte is shown in FIG. 4. The apparatus 90 is similar to the apparatus 20 of FIG. 1. In particular, the apparatus 90 includes a support assembly 92, a load assembly 94, an electrophoresis assembly 96 and a controller 110 that operate in manners similar to those of the apparatus 20 as will now be explained.

The load assembly 94 loads samples onto test modules 32 that are received and supported by the support assembly 92.

The load assembly 94 includes a fluid transfer device 100 and a robotic device 102 that moves the fluid transfer device 100 in a manner similar to that of the robotic device 36 of FIG. 1. The fluid transfer device 100 (e.g., a multi-tip pipetter) is capable of transferring multiple sample sources 104, in parallel/simultaneously, to one or more test modules 32. Additionally, the fluid transfer device 100 may operate as an injection device to preload the test modules 32 with fluid prior to sample loading. Accordingly, there is no need for a separate injection assembly (as shown in FIG. 1).

The apparatus 90 further includes a wash station 98 that washes the fluid transfer device 100 between sample transfers to avoid contamination between the samples. The wash station 98 preferably washes the fluid transfer device 100 before and after each of the fluid injection and sample loading procedures.

The apparatus 90 may further include other features of the apparatus 20 of FIG. 1. In particular, the apparatus 90 may include a detection assembly 106 which resides below the test modules 32. In a manner similar to the detection assembly 80 of FIG. 1, the detection assembly 106 of FIG. 4 moves relative to the test modules 32 and the support assembly 92 to selectively scan the test modules 32 (i.e., multiplex between the test modules 32) after electrophoresis.

Preferably, the load assembly 94 of the apparatus 90 includes a camera 108 that sends an alignment signal to the controller 110. The alignment signal indicates the position of the camera 108 and the fluid transfer device 100 relative to positions on the support assembly 92 (e.g., positions over the sample sources 104 and the test modules 32). The controller 110 moves the fluid transfer device 100 robotically between the sample sources 104, the wash station 98 and the test modules 32 according to the alignment signal. In particular, the controller 110 provides a robot signal to the robotic device 102 to control the movement of actuators of the robotic device 102.

Within the test module 32 is a microchip (also called an "ME device"). It should be understood that the automated features of the apparatus 90 of FIG. 4 (as well as the apparatus of FIG. 1) provide a bridge between the conventional macroscopic format (millimeter geometries) of microtitre plates and the microscopic (micrometer geometry) format of ME devices. That is, the current invention solves this problem by close integration of a precision motion control system with the ME device. Both the motion control system and the ME device are specifically customized with microfabricated structures to achieve an efficient overall solution to the required format change.

Further details of the fluid transfer device 100 will now be discussed. The apparatus 90 of FIG. 4 accurately translates a precision manufactured fluidic transfer head of the fluid transfer device 100 which transfers microliter fluid quantities. An optical system (the camera 108) is mounted on the load assembly 94, and computer hardware and driver software of the controller 110 control the motion of the fluid transfer head allowing it to perform pre-programmed, automated repetitive procedures. Affixed to an active arm of this fluid transfer head is a multi-tip array of specialized fluid-handling tools 110 capable of collecting and dispensing microliter amounts of fluid accurately and reproducibly. The robotics and associated optics serve to align and position the tip array over an industry-standard multiple-well microtitre plate and collect the desired amount of liquid sample. The motion system then lifts the tip array to the ME device of the test module 32, aligns to the ME device using the robotic optics system described above, and instructs high-precision pumps to dispense the samples from the tip array into the appropriate microfabricated injection ports (each approximately 100 $\mu$m in diameter) on the ME device of the test module 32. This cycle is repeated until all of the injection ports on the ME device of the test module 32 have been loaded. Accordingly, the automated features of the apparatus 90 solve the format transformation problem by bridging the conventional macroscopic format (millimeter geometries) of microtitre plates with the microscopic (micrometer geometry) format of microchips of the test modules 32.

Once the ME device is loaded, the electrophoresis assembly 96 separates the samples based on their molecular weight and mobility through a microchip sieving medium. In one embodiment, an optical laser-induced fluorescence system is used to excite fluorescently tagged molecules. The resultant signal is collected by a series of optics and photomultiplier tubes or charge-coupled device cameras in the detection assembly 106 and analyzed using software appropriate for the separation being done.

Figure 5:
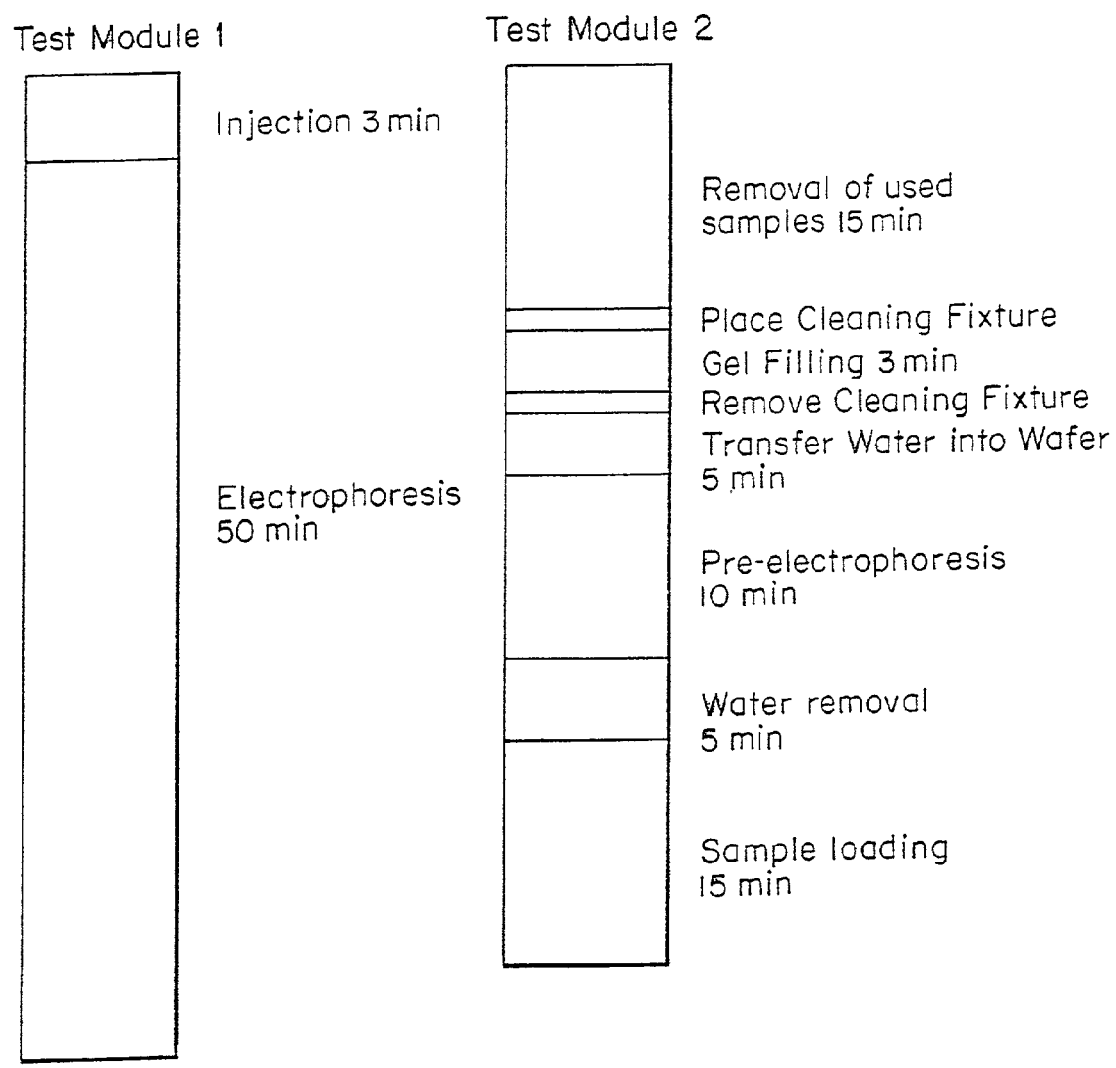
FIG. 5 is a timing diagram of the operation of the system of FIG. 2.

It should be understood that the apparatus 20 of FIG. 1 and the apparatus 90 of FIG. 4 support the use of multiple test modules 32 (each test module 32 being capable of simultaneously testing multiple samples itself). In particular, the apparatus 20, 90 can perform electrophoresis on one test module 32 while preparing another. FIG. 5 shows a timing diagram for two test modules 32 used by the apparatus 20 of FIG. 1 and by the apparatus 90 of FIG. 4. As shown, while a first test module 32 undergoes injection and electrophoresis, another test module undergoes other procedures such as sample removal, cleaning and sample loading. As a result, the various assemblies of the apparatus 20, 90 are multiplexed between the multiple test modules 32.

Figure 6:
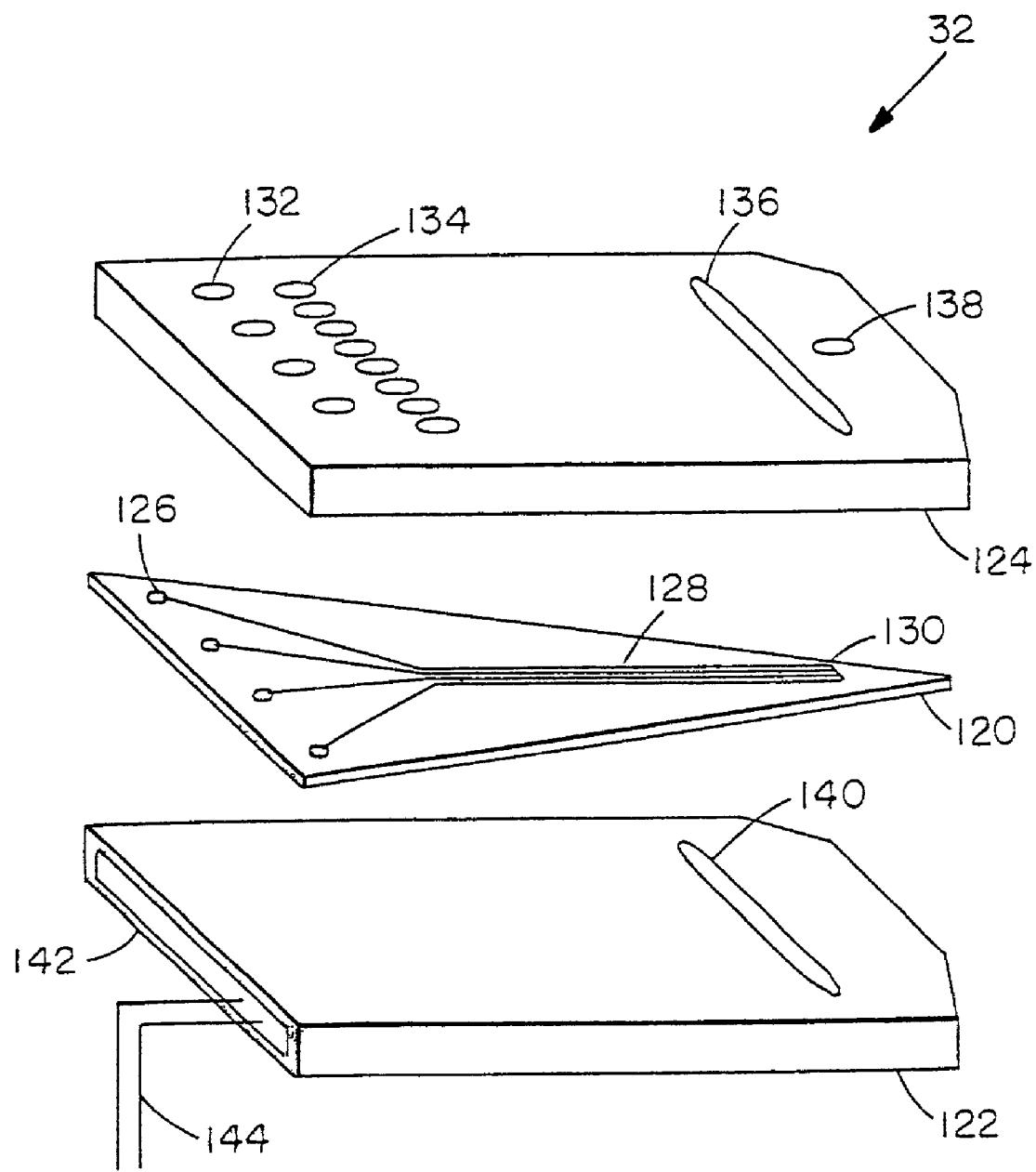
FIG. 6 is an exploded view of a test module that is usable by the systems of FIGS. 1 and 4.

Further details of the test module will now be provided with reference to FIG. 6 which shows an exploded view of a test module 32. The test module 32 includes a microchip 120, a lower housing member 122 and an upper housing member 124. The lower and upper housing members 122, 124 form a housing that protects and supports the microchip 120. The microchip 120 is planar in shape with a top surface (an upper planar surface) and a bottom surface (a lower planar surface) spaced apart from the top surface. The microchip is preferably wedge (or triangle) shaped. One end of the top surface has a set of injection ports 126 that operate as target openings that receive injection fluid, test samples and electrophoresis electrodes. The microchip 120 includes channels 128 that extend within the microchip 120 along a plane with the planes of the microchip 120 surfaces. The top surface of the microchip 120 further includes additional openings 130 that allow air to escape when material is injected into the channels 128 and to provide access for additional electrophoresis electrodes.

The upper housing member 124 has a set of openings 132 that match the target openings 126 of the microchip 120. The openings 132 provide access to the target openings 126 when the upper housing member 124 covers the microchip 120. In a similar manner, the upper housing member 124 has other openings 134 and 138 to provide access (e.g., light and electrophoresis electrodes) to the microchip 120 when the microchip is housed by the housing members 122, 124.

The upper housing member 124 further includes a slot 136 and the lower housing member includes a corresponding slot 140. The slots 136, 140 allow light to pass from one slot to the other through the microchip 120 when the microchip 120 is housed by the housing members 122, 124. This allows a detection assembly to scan particular areas of the channels 128 within the microchip 120 after (or during) electrophoresis. In particular, the matching slots 136, 140 provide optical access for laser-induced fluorescence detection.

The lower housing member 122 further includes a heating element 142 (a heater) that provides heat to the microchip 120 when power is provided to the heater through electrical connections 144 (e.g., high-voltage connections) of the heating element 142. The heat facilitates STR separation within the channels 128. Preferably, the heating element 142 is a ceramic device with high thermal conductivities (above 10 Watts/(meter Kelvin)) and high dielectric strengths (above 50 volts per mil). Alumina, beryllia, and boron nitride ceramics are suitable for the ceramic device.

Figure 7:
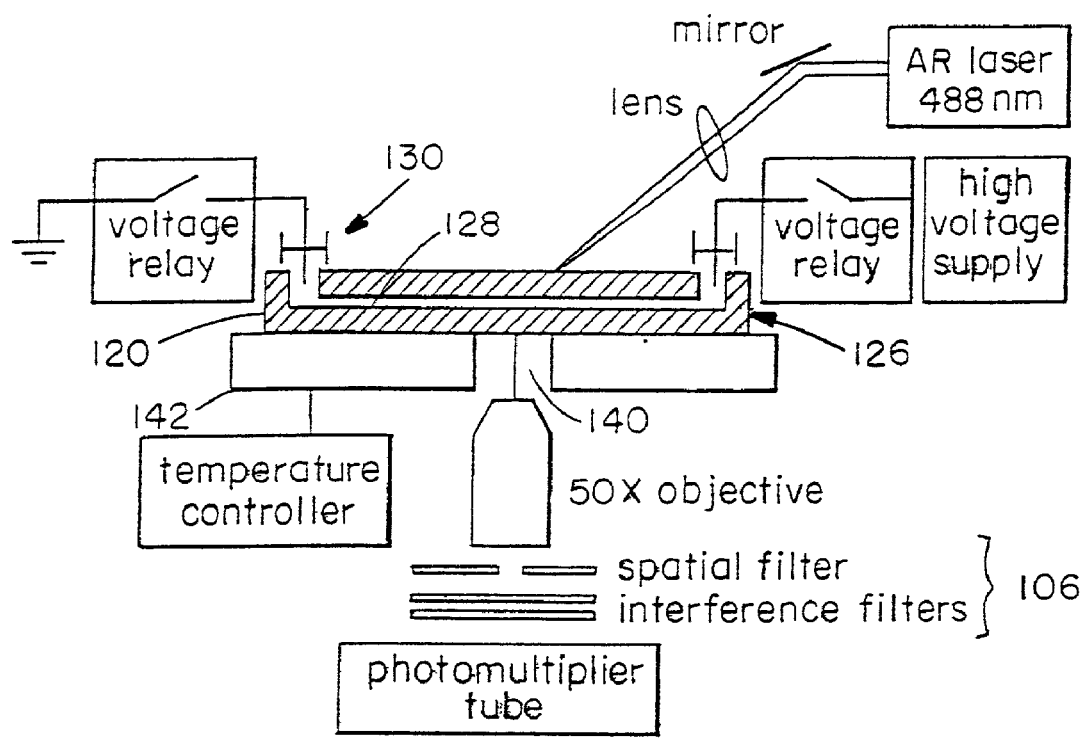
FIG. 7 is a side view of a test module when in use by one of the systems of FIGS. 1 and 4.

FIG. 7 provides a schematic view of a test module 32 (FIG. 6) disposed on the apparatus 90 of FIG. 4. Electrophoresis electrodes are connected at the openings 126, 130 of a channel 128 of the microchip 120. The electrodes lead to a power supply through voltage relays that are switchably controlled by the controller 110 (see FIG. 4). The controller 110 further provides temperature control for the heating element 142 (heater block). Additionally, the detection assembly 106 (scanner and laser) scans a portion of the channel 128 of the microchip 120 to record STR separations.

Figure 8A:
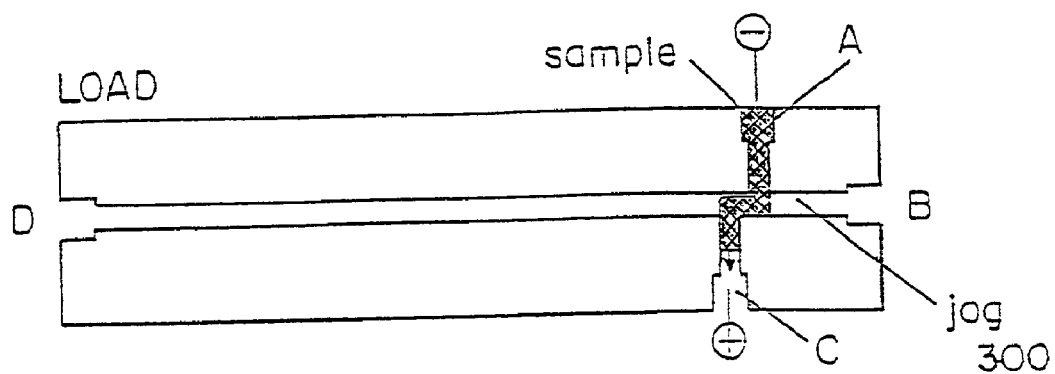
FIGS. 8A–8C are top view portions of a microchip that is suitable for use by the systems of FIGS. 1 and 4.
Figure 8B:
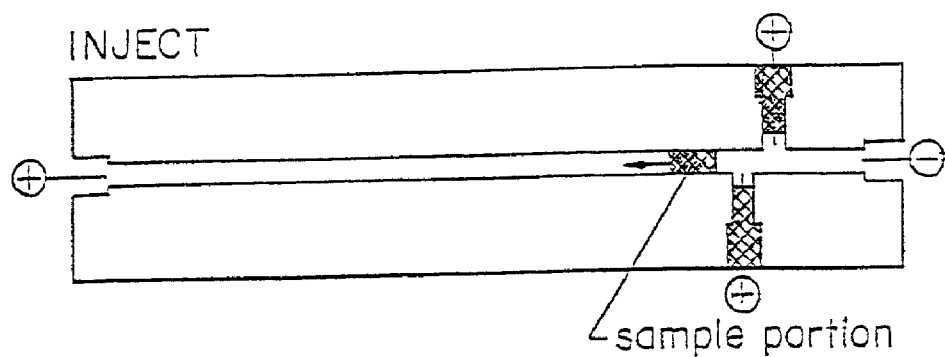
Figure 8C:
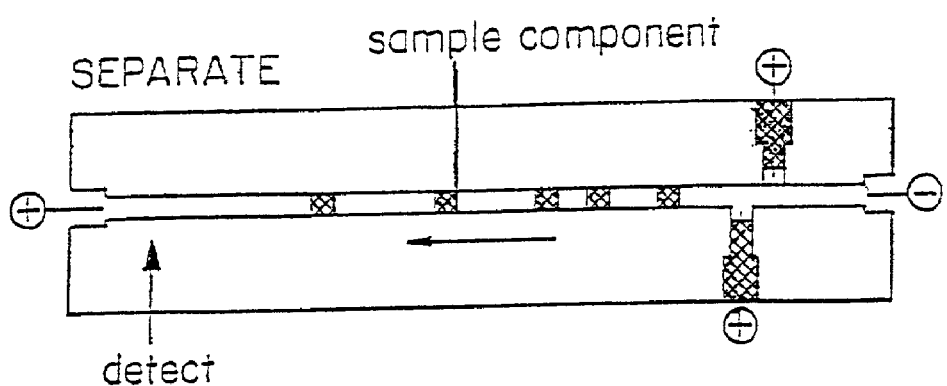

Further details of the microchip 120 of the test module 32 will now be provided with reference to FIGS. 8A, 8B and 8C, which provide various partial top views of the microchip 120. The microchip 120 includes multiple sets of channels 128, one set being shown in each of FIGS. 8A–8C. Each set of channels (or channel set) includes an injection channel 150 and a separation channel 152. The injection and separation channels 150, 152 of each set 128 are coplanar with the plane of the microchip 120. The separation channel 152 is longer than the injection channel 150 and intersects the injection channel 150 at a right angle (90 degrees). The injection channel 150 has a jog 300 where it intersects the separation channel 152 to allow precise control of the amount of sample to be separated within the separation channel 152.

Further explanation of the electrophoresis operation will now be provided. First, a load assembly injects a sample into the injection channel 150 at the negative electrode end, as shown in FIG. 8A. Second, an electrophoresis assembly performs electrophoresis along the injection channel 150 causing the sample to partially migrate and separate in the direction of the positive electrode. A portion of the sample becomes positioned within the jog 300 during electrophoresis along the injection channel 150. Next, as shown in FIG. 8B, the electrophoresis assembly performs electrophoresis along the separation channel 152. The portion of the sample within the jog 300 travels down the separation channel 152 and separates further. Other portions of the sample remain in the injection channel 150. The particular amount of sample separated in the separation channel 152 can be precisely controlled by the diameter of the separation channel and the length of the jog 300. Then, as shown in FIG. 8C, the portion of the sample separates into components along the separation channel 152 as electrophoresis continues along the separation channel 152. In particular, movement of the components within the separation channel 152 is from the negative electrophoresis electrode (at one end of channel 152) to the positive electrophoresis electrode (at the opposite end of the separation channel 152). Since very large components of the sample remain in the injection channel 150, component separation within the separation channel 152 is less hindered. Finally, the separated components can be detected near the end of the separation channel 152 having the positive electrode.

In one version of the microchip 120, the injection channel 150 is 10 mm in length and the separation channel 152 is 35 mm in length. The separation channel 152 divides the injection channel 150 into two 5 mm portions, and the injection channel 150 divides the separation channel 152 into a 5 mm portion and a 30 mm portion.

To create more compact structures in the microchip 120, the geometry of the separation channel 152 can be extended in length and folded. For example, the separation channel 152 can have a folded channel that is approximately 100 mm in length, or even approximately 300 mm in length.

Conventionally, the injection channel 150 extends along a plane that is coplanar with that of the microchip 120 surfaces in the same manner as the separation channel 152. Accordingly, when the microchip 120 is disposed horizontally during electrophoresis, the injection channels 150 and the separation channels 152 are perpendicular with the direction of gravity. In this arrangement, all of the openings in the microchip are on the top surface of the microchip 120.

Figure 9A:
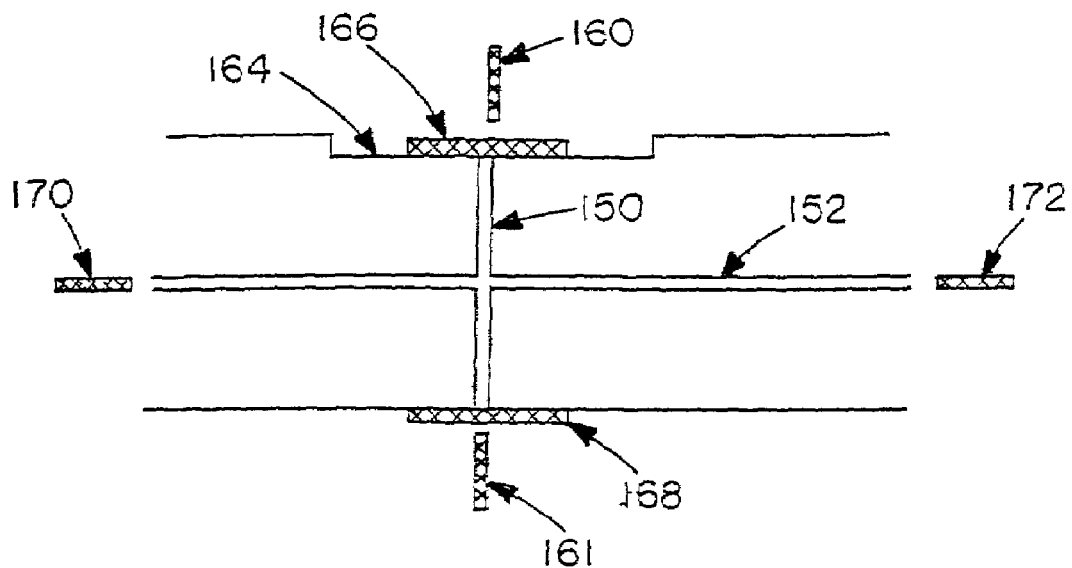
FIGS. 9A and 9B are views of a preferred microchip that is suitable for use by the systems of FIGS. 1 and 4.
Figure 9B:
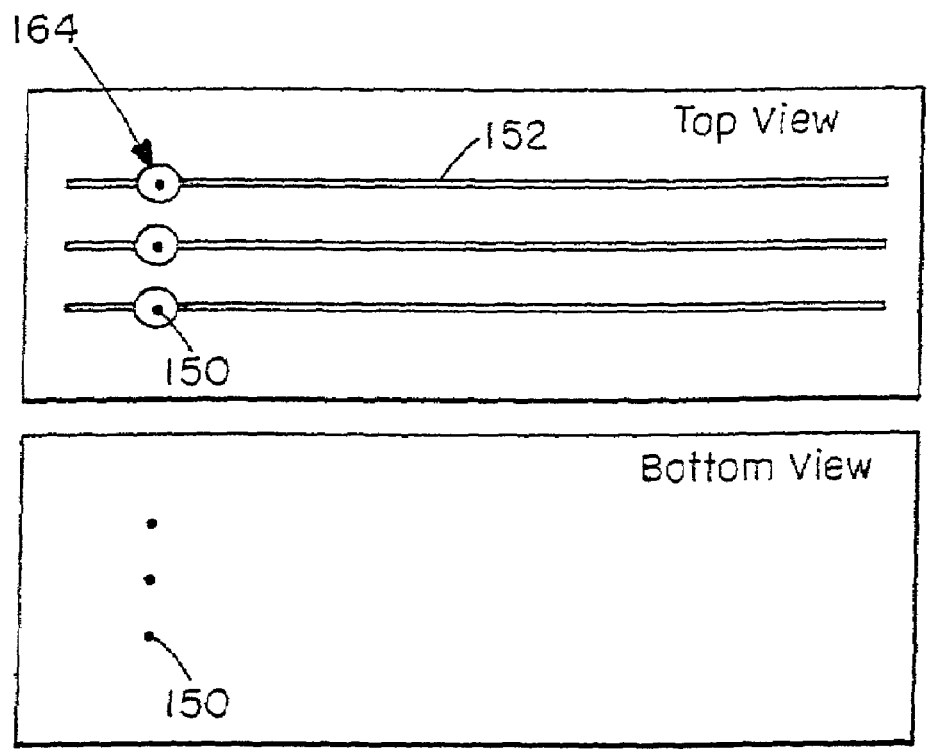

In a preferred microchip embodiment, the separation channels extend along a plane that is coplanar with the surfaces of the microchip in a manner similar to that of conventional separation channels. However, in the preferred embodiment, the injection channels extend from the top surface to the bottom surface of the microchip and are orthogonal to the plane of the microchip surfaces, as shown in FIGS. 9A and 9B. That is, the opening of the injection channel 150 that receives the sample and provides access to an electrophoresis electrode 160 (i.e., the injection port) is at the upper surface, and the other opening that provides access to another electrophoresis electrode 161 is at the bottom surface. When the microchip 120 is oriented such that its plane is horizontal (i.e., perpendicular to the direction of gravity), the injection channel 150 of the preferred embodiment is oriented in the vertical direction (i.e., with the direction of gravity). Preferably, the injection channel is at right angles with the top and bottom surfaces of the microchip 120.

The microchip 120 may include a well-shaped indentation 164 around the injection port opening, as shown in FIG. 9A. The indentation helps hold the sample over the receiving port of injection channel 150 when the sample is introduced to the microchip 120. Preferably, porous membranes 166, 168 cover the openings of the injection channel 150 to hold the injection fluid (i.e., a separation matrix) within the injection channel 150. The membranes 166, 168 can be adhered to the microchip 120. The pores of the membranes 166, 168 should be small enough to prevent the injection fluid from passing through. Suitable membranes include polyvinylidene fluoride membrane filters (either hydrophylic or hydrophobic types) with pore sizes of 0.1 micron to 0.65 micron, and polytetrafluoroethylene membrane filters of 0.2 to 5.0 micron pore sizes. Such filters are available from Millipore Inc. of Bedford, Mass. Also shown in FIG. 9A are the electrophoresis electrodes 170, 172 for the separation channel 152.

FIG. 9B shows top and bottom views of a preferred geometry microchip 120 having three sets of channels. The top view shows the indentations 164 in the top surface of the microchip 120 for each set of channels. Although the separation channels 152 are shown extending along the microchip 120, the injection channels 150 are shown on end in both the top and bottom views.

It should be understood that the vertical orientation of the injection channels 150 permits the channel sets to be densely clustered on a simple microchip 120. In particular, more channel sets with vertical injection channels are able to be clustered in a microchip area than channel sets with non-vertical injection channels. Accordingly, more samples can be separated in a particular microchip area, and more separation channels can be scanned by a detection assembly without having to substantially move the detection assembly relative to the microchip.

Furthermore, it should be understood that the vertical injection channel of the microchip of FIGS. 9A and 9B may have a geometry similar to the horizontal injection channel FIGS. 8A–8C. That is, the vertical injection channel may include a jog where it intersects the separation channel such that a cross-section of the vertical injection channel microchip looks similar to FIGS. 8A–8C.

Figure 10:
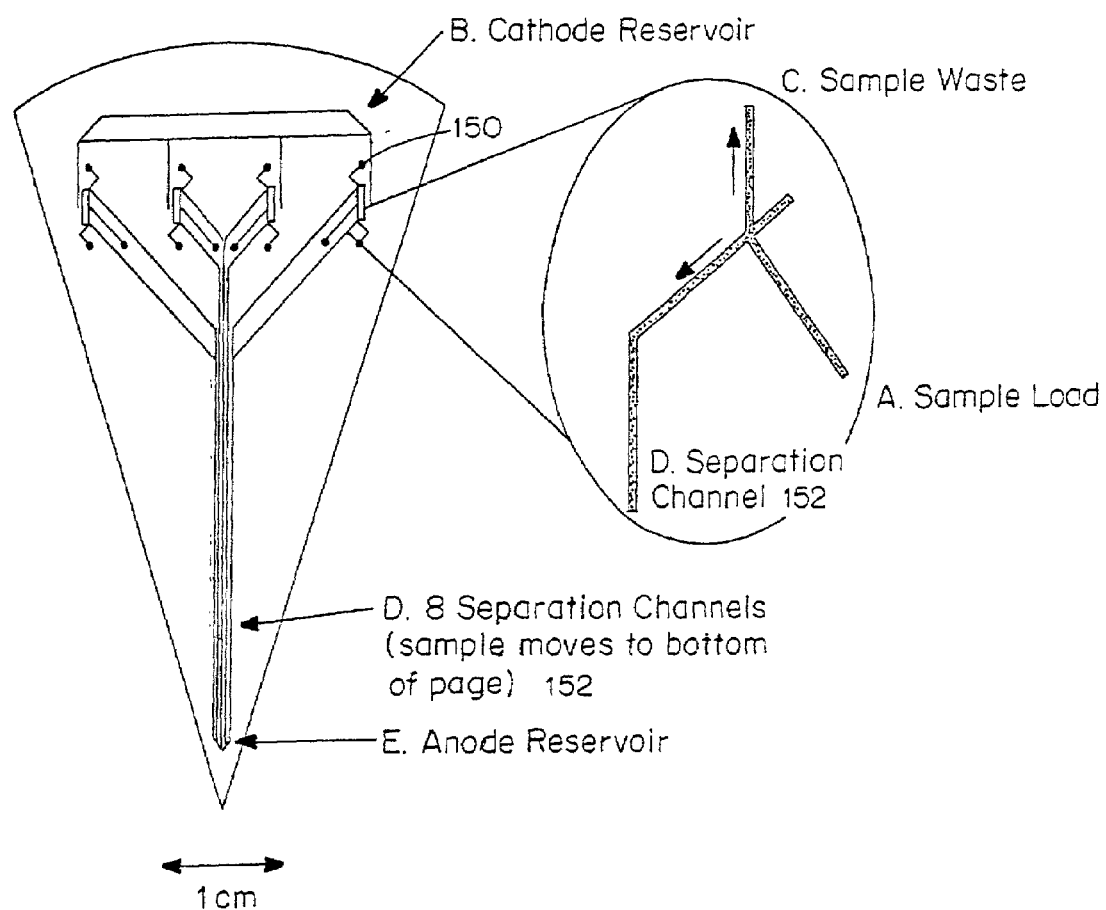
FIG. 10 is a top view of the preferred microchip of FIGS. 9A and 9B.

FIG. 10 shows a preferred arrangement of channel sets on a wedge-shaped microchip 120. The injection channels 150 are spaced apart to provide enough room for samples to be injected into the injection ports without risk of sample cross-mixing between injection ports. Such spacing is on the order of millimeters which is less suitable for human load handling than the automated loading means discussed above in FIGS. 1 and 4. The separation channels 152 are allowed to be spaced more closely together to enable simultaneous scanning at the narrow end of the wedge shape.

Figure 11A:
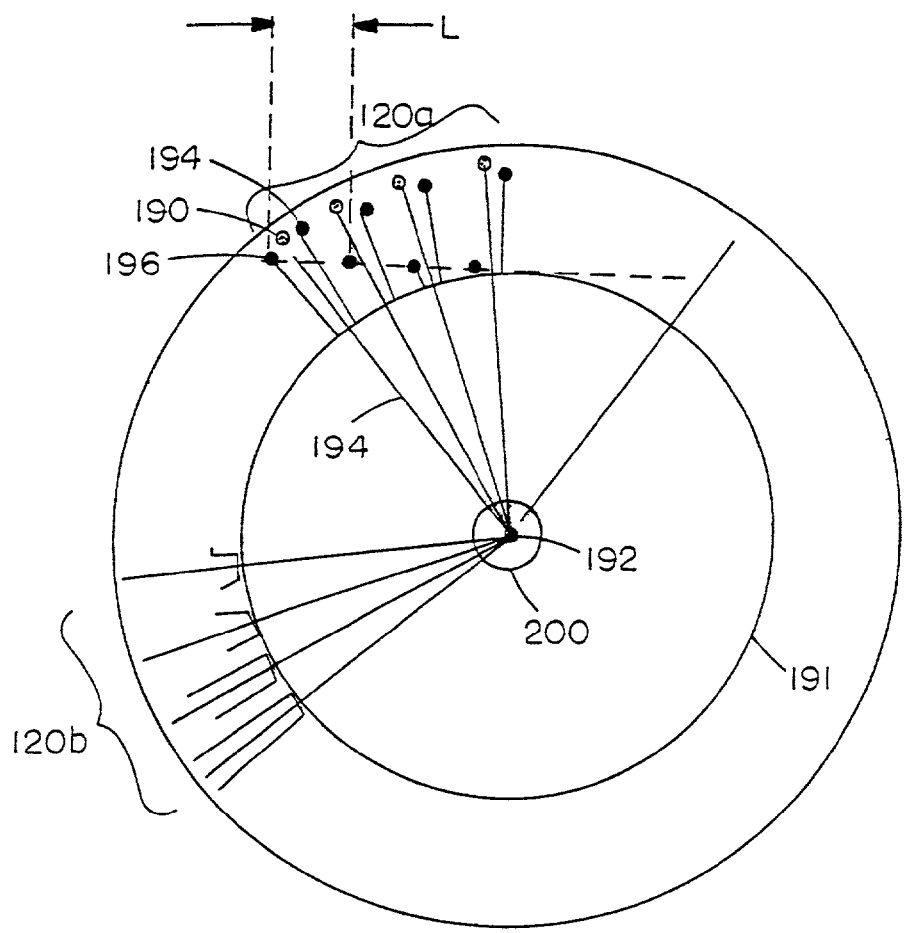
FIGS. 11A and 11B are perspective views of a scanning arrangement for scanning a microchip that is usable by the systems of FIGS. 9A, 9B and 10.

As stated above in connection with the apparatus 20 of FIG. 1 and the apparatus 90 of FIG. 4, the detection assembly may move between test modules 32 to multiplex the use of a single scanner. Alternatively, the wedge-shaped microchip 120 may be positioned in a pie-shaped fashion on a platter 191 with other wedge-shaped microchips 120a, 120b, . . . in a rotary configuration, as shown in FIG. 11A. The platter 191 rotates beneath a detection assembly 202 such that portions (along line 200) of each wedge-shaped microchip pass by detection assembly for scanning, as shown in FIG. 11B.

Figure 11B:
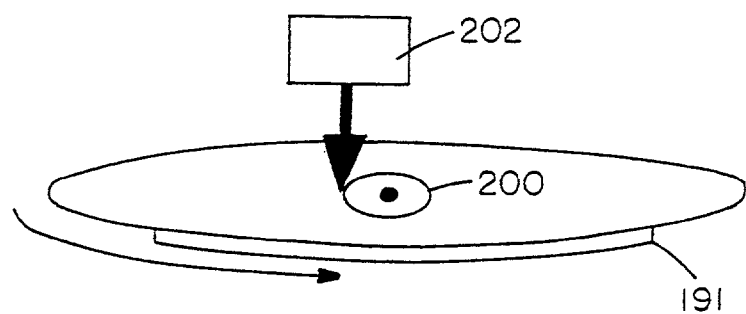

Another version of the microchip 120 has a rotary geometry to simplify loading and detection (also see FIGS. 11A and 11B). The chip is a single rotatable disk shaped structure with embedded channels 194. The channels 194 are radially disposed, and extend inwardly to terminate at the same point. Samples are electrophoretically driven radially toward the center of the disc from electrode wells 190 to electrode well 192. Samples are injected by introducing samples at wells 194 driving them toward wells 196, followed by a switching operation. In one mode of use, the device is spun under (or over) a single point detector or the detector is spun under (or over) the device. The detector then scans a circle of detection zones 200 near the center of the device. In this geometry the channels 194 are arranged in a radial pattern around a disc. The electrophoresis current is arranged to run from the periphery of the disc toward the disc center. During sample loading, the disc is rotated in a stepwise fashion and the robotic arm with its multi-tipped sample transfer arm is brought from the sample tray to the disc as illustrated in the figures. In principle this eliminates one axis of motion that would otherwise be needed for the load robot. In one embodiment of the read-out method, the disc is spun continuously during the electrophoresis run. A laser fluorescent or similar detector 202 remains aimed at a stationary point, for example, at several millimeters radius from the chip center. The rotary rate of the disc revolution is keyed to the gating period of the detector, so that the signal from each channel is synchronized with the data acquisition. This permits data from multiple channels to be multiplexed in time from a single detector.

Referring to FIGS. 11A and 11B, consider the case of loading samples from an industry-standard 96-well micropipet plate. A pipet head with 8 tips arranged in a linear array with 9 mm spacing would be put on a robotic arm. The arm must have two linear axes of motion, X and Z, so as to permit the pipet head to pick up 8 samples and to then deposit them into 8 wells on the rotary chip, also spaced at 9 mm center. This arrangement is possible, for example, by using a 5 inch diameter chip and by arranging sample load ports in linear arrays with 9-mm well spacing around the periphery of the disc. If 24 arrays of 8 wells are arranged around the 5-inch disc then a total of 192 lanes can arranged on a single disc. The chip is loaded with a total of 24 robotic cycles. During the read-out, for example, the disc can then be spun at a rate of 600 rotations per minute (10 rotations per second). The laser point detector will then be able to read each channel at the rate of 10 readings per second.

It should be understood that the apparatus of FIGS. 1 and 4 with test modules 32 form microelectrophoresis systems for processing biomolecular analyte (e.g., portions of DNA such as STRs) with improved throughput over conventional systems. These systems provide means for order-of-magnitude improvements in parallelism and reductions in cost through a fully integrated process flow organized around a microchip, i.e., a unique microchannel device preferably having a vertical injection channel. Each microchip can support a channel set lane density (i.e., the number of channels per unit area) greater than 30 lanes per centimeter. The vertical injection channel enables scaling of the injected sample to less than 100 nanoliters, including a sample of less than 10 nanoliters and of less than 5 nanoliters. Analysis of simple DNA typing can be carried out rapidly (e.g., in 30 seconds or less). In addition, the reduction in required sample injection permits very substantial (order of magnitude) reductions in the consumption of expensive reagents such as enzymes.

The DNA typing procedure performed using the apparatus of either FIG. 1 or FIG. 4 involves an allelic profiling assay for the analysis of STRs which can be carried out more rapidly than is possible using conventional methods and capillary or slab gel systems. Such a procedure makes it possible to genotype a single STR locus in 30 seconds or less and to rapidly analyze an STR system consisting of multiple loci (e.g., to analyze an STR system consisting of 4 loci in less than 2 minutes).

In one embodiment, the microchip is microfabricated to produce channel structures which can contain an injection plug whose width is 100 $\mu$m or less. The narrow injection plugs result in short separation devices and, therefore, shorter analysis times and reduced diffusion. In one embodiment, the injection plug width is about 100 $\mu$m or less, such as between 75 $\mu$m and 100 $\mu$m, between 50 $\mu$m and 100 $\mu$m, between 25 $\mu$m and 75 $\mu$m, between 25 $\mu$m and 50 $\mu$m or between 25 $\mu$m and 100 $\mu$m. In a particular embodiment, the separation device includes a microfabricated channel of about 45 $\mu$m×100 $\mu$m in cross section and about 20–30 mm (e.g., 26 mm) in length. The channel is filled with a replaceable matrix (injection fluid), such as a replaceable polyacrylamide matrix, which is operated under denaturing conditions at a temperature of about 50° C.

As will now be explained, particular components of the apparatus of FIGS. 1 and 4 are available as over-the-counter parts. For example, for the apparatus 90 of FIG. 4, the load assembly 94 may use a gantry-style XYZ robotic motion system operating with linear brushless motors in the X,Y axes, with 500×800 mm travel and 5-$\mu$m (Aerotech Incorporated, Pittsburgh, Pa.). The Z axis can be controlled with a DC servo motor to 2 micron accuracy (25 mm travel). The camera 108 may be implemented with an optical system (Edmund Scientific, Inc.) mounted on a tool platform of the load assembly 94. Motion may be programmed using a PC (Compaq, Inc.) and driver software (Aerotech, Inc.) to control the motion of the robot and allow it to perform pre-programmed, automated repetitive procedures. Affixed to the tool platform of load assembly 94 can be an array of eight stainless steel fluid handling tips 100 (Hamilton, Inc, Reno, Nev.), fixed on 9 mm centers in order to match the microtitre well spacing, coupled via 0.030 inch outer diameter Teflon tubing to high-precision pumps (Cavro Instruments, Inc., Sunnyvale, Calif.). Each tip may be placed into a relative position with an accuracy of plus or minus 2 mils.

In connection with the test module 32, once the microchip is loaded, the electrophoretic separation can be implemented to separate components within the samples based on their molecular weight and mobility. In particular, separation through the ME device sieving medium can be implemented by applying a series of switched DC fields to draw analyte down the microfabricated channel of the ME device. The bias applied can be 100 to 800 volts per cm of channel length. An optical laser-induced fluorescence system (Omnichrome, Inc.) can be used to excite fluorescently tagged DNA samples (e.g, CCTV forensic diagnostic samples, Promega Corp.) During electrophoresis the resultant signal can be collected by a 50x microscope objective (Bausch and Lomb, Rochester, N.Y.) and photomultiplier tube (I P28, RCA Corporation) and by a charge-coupled device (Princeton Instruments, Inc., Princeton, N.J.) and analyzed using software appropriate for the separation being done. Dichoic filters can be used to collect signal and to reject laser light, using methods known to those skilled in the art of capillary electrophoresis.

It should be understood that the robotic devices of the apparatus in FIGS. 1 and 4 are capable of moving the tip array of the fluid transfer devices with complete degrees of motion (x-, y-, z-motion). The purpose of this arrangement is two-fold; first, to collect microliter and sub-microliter amounts of fluid sample from industry standard microtitre plates and subsequently position and dispense these samples onto the microfabricated vertical injection ports of the ME device and to provide support for (or even serve as) one set of electrodes. This device structure is used in combination with a robotic fluid handling system to provide ultra-high-density sample injection into the ME device.

Further details of the operation, preparation and manufacture of the vertical injection channel microchip will now be provided. The vertical injection channel has two well-aligned holes leading to the top and bottom surfaces of the microchip, as shown in FIGS. 9A and 9B. The sample material is put in contact with the top hole, and an electrophoretic current is drawn from top to bottom using electrodes. Once the sample stream is well established in this vertical injection channel, the sample trapped at the intersection of channels and is switched so as to move down the separation channel. This is accomplished by switching the electrophoresis current so as to drive the sample volume from the intersection of the channels and down the (horizontal) separation channel, i.e., from one electrode of the separation channel to another electrode of the separation channel. Preferably, the top plate is coated on its exterior surface with a hydrophobic agent. The indentation well 164 is treated with a hydrophilic substance to greatly alleviate the robotic positioning of sample.

To form the vertical injection channel microchip, two fused silica plates 180, 182 micrometers thick from Hoya Corporation are prepared in the geometry of FIGS. 9A and 9B. Channel structures 150, 152 and indentation wells 164 are etched into the top plate 180 using photoresis (Shipley Corporation) to pattern an evaporated chromium layer. Using this chromium layer as a masking layer, 50 micrometer-deep structure was etched into the top plate 180 with a $NH_4F/HF$ (1:1) etchant at 50° C. A $CO_2$ laser system is then used to create 75 micrometer vertical channels 150 through the process of laser ablation on both top and bottom plates. Following the laser ablation step, both top and bottom plates 180, 182 are briefly etched in the $NH_4F/HF$ (1:1) etchant for 60 seconds. This leaves the surfaces of both plates in a hydrophobic condition.

Approximately 400 microliters of sieving gel (either 2% linear polyacrylamide of 5,000,000 molecular weight dissolved in TAPS buffer, or hydroxyethylcellulose dissolved in TAPS buffer) is placed between the two plates 180, 182, each measuring approximately 45 $cm^2$ in area. The two plates 180, 182 is carefully aligned and compressed together. This protocol succeeds in sealing the microfabricated channels and maintaining the sieving gel intact within them. No cross-contamination of adjacent channel sets as close as 200 $\mu$m is evident with this procedure.

A fluorescein-labeled PCR primer (Perkin-Elmer Corp.) Is introduced through the indentation well 164, and the switched electrophoresis protocol described above is conducted at an injection voltage of 200 volts per centimeter of channel length. In one embodiment, an argonion laser operating at 488–514.5 nm wavelength is used in combination with a filtered photomultiplier tube as a detector in the manner well understood by those skilled in the art of electrophoresis.

The precision of the motion system is significantly relaxed using the concept of a hydrophobic moat. According to this concept, the bulk of the top ME device surface may be treated to form a hydrophobic surface, and the sample loading wells 164 are coated or filled with a hydrophilic substance. As a result, fluid dispensed by the fluid transfer system is selectively attracted to the loading wells. In one embodiment of the hydrophobic moat concept, the ME device is briefly etched in a hydrofluoric-acid-based etching solution to create a hydrophobic top surface. The microchip is then injected with polyacrylamide solution (which is hydrophilic), and a small layer of this injected material is left in the indented wells 164. Those skilled in the art will know of alternative methods of treating ME device structures so as to achieve local areas of hydrophilic and hydrophobic character.

In one embodiment in which the microchip is designed to achieve 3 channel per millimeter channel density, channels of 50 micron width are etched at 333 micrometer spacing and terminated with sample wells of 500 micron diameter in a staggered array. The accuracy of the placement of samples is therefore relaxed by one order of magnitude from about 50 microns to about 500 microns. Relaxing the positioning accuracy and cost of the motion system robotics reduces set-up time when replacing the ME device.

In one embodiment of the invention, electrically conducting stainless steel tips (Hamilton Corporation, Reno, Nev.) of inner diameter 150 $\mu$m and outer diameter 720 $\mu$m set in a linear array on 4.5 mm or 9 mm centers, matching the well-to-well spacing of currently used industry-standard microtitre plate wells. These tip arrays have been attached to a robotic system, operated with proper software protocols, which have successfully placed them within 10 $\mu$m of the injection ports on quartz ME devices, well within the tolerances of successful loading into the 100 $\mu$m diameter injection port size.

Further details of the fluid transfer device 42 of FIG. 2 will now be provided. The fluid transfer device 42 is based on the well-known solid-phase reversible immobilization (SPRI) technique introduced by Hawkins et al. (Hawkins et al., 1994) by which single-stranded DNA is bound to paramagnetic 1 μm iron oxide spheres (Bangs Laboratories Estaphor M0008801CN) under 13% polyethylene glycol 8000 (PEG) and 10 mM $MgCl_2$ salt concentrations (Paithanker and Prasad, 1991). Following binding of DNA to the paramagnetic spheres in an industry-standard microtitre plate, the assembly shown in FIG. 2 is used to transfer the DNA and spheres into the microchip, where the DNA is subsequently washed, eluted, and denatured in situ inside the microchip.

In FIG. 2, a nickel wire (the core 52) is embedded in a non-magnetic cylindrical piston. The piston/wire assembly is positioned in a non-magnetic housing such that motion of the cylinder in the x- and y- directions is minimal. The nickel wire is magnetized by applying a current to solenoid coils (the winding 54) which surround a portion of the nickel wire. Once magnetized, the iron oxide beads coated with the ssDNA adhere magnetically to the exposed nickel wire tip 58. The fluid transfer device 42 is then precisely positioned over the injection port of the microchip of test module 32, and the exposed nickel wire tip is inserted into this entrance port. A compressed spring and hard stop allow retraction of the tip in case of unintended or unsuccessful placement without damage to the ME device or wire tip. An electromagnet positioned underneath the microchip is then energized while the solenoid in the assembly is de-energized, and the ssDNA-coated beads are thus held inside the injection port vicinity inside the NM device. While magnetically held in place, the ssDNA beads are then subsequently washed, eluted, and denatured. The released DNA is then electrophoresed and separated in the separation channel of the ME device, while the now uncoated magnetic beads are held in the injection port area by the electromagnet. Methods of denaturing the ssDNA after they have been released from the beads include increasing the temperature of the ME device with an external heating unit, or pulsing the current through the electromagnet to induce local heating in the vicinity of the injection port. Initial experiments with such a nickel wire system coupled to a solenoid successfully demonstrated collection of paramagnetic μm iron oxide spheres (Bangs Laboratories Estaphor M0008801CN); the solenoid ted of approximately 500 turns of copper wire carrying 200 mA with an inner air core diameter of 5 mm, and a 0.005 inch diameter piece of wire approximately 1 cm in length.

The present invention is further illustrated by the following examples, which are not intended to be limiting in any way. The examples are similarly described in an article entitled "DNA typing in thirty seconds with a microfabrication device", by Schmalzing et al., Proc. Natl. Acad. Sci. USA, Vol. 94, pp. 10273–10278, September 1997, Genetics, the teachings of which are hereby incorporated by reference in their entirety.

EXAMPLES

Methods and Materials

The following methods and materials were used in the examples described herein.

Micromachining. Miniaturized electrophoresis devices were fabricated using photolithography and chemical etching methods to produce channel structures in fused silica wafers. A 40-nm-thick film of chromium was sputtered onto 150-mm-diameter 0.4-mm-thick fused silica wafers (Hoya, Tokyo, Japan). 1811 Photoresist (Shipley, Marlborough, Mass.) was spin-coated onto the wafer to a thickness of 1.1 mm and baked at 90° C. for 25 minutes. The resist was patterned by selective exposure to 365-nm UV light (UVP, Upland, Calif.) through a contact photomask with linewidths of 10 μm (Advanced Reproductions, Wilmington, Mass.) and developed with Microposit photoresist developer (Shipley). The selectively exposed chrome was removed using $K_3Fe(CN)_6$/NaOH chrome etch (Shipley). The resulting mask pattern was etched into the fused silica by immersing the wafer in $NH_4F$/HF (1:1) etchant at 50° C. The depth of etching was controlled by monitoring etching time and measured with a profilometer. Photoresist was removed with acetone, and the remaining chrome was dissolved using $K_3Fe(CN)_6$/NaOH. Access to the channel ends was provided by 75-mm-diameter holes drilled through the etched wafer with a $CO_2$ laser system. A second 150-mm-diameter fused silica wafer was contact bonded to the etched wafer to enclose the channels. To achieve bonding, both wafers were immersed in a bath of $NH_4OH/H_2O/H_2O_2$ 4:5:1 at 50° C. and then rinsed thoroughly with filtered water. They were then placed in direct contact and thermally bonded. Initial reversible bonding took place at 200° C. (2 h), followed by final permanent bond formation at 1000° C. overnight. This is well below the softening point of the fused silica substrate utilized and, therefore, the bonding is due to the formation of covalent bonds between the two surfaces and not diffusion of boundary molecules. Individual microchips were cut from the bonded wafer pair using a wafer saw. Reservoirs of 50 microliters volume were formed by affixing 5-mm-tall 3-mm-i.d. glass raschig rings (Ace Glass, Vineland N.J.) with optical cement (Norland Optical, New Brunswick, N.J.) around each exit hole.

Reference is made to a cross-structure device with a straight separation channel in FIG. 8A. Portions of the injection channel 150 and the separation channel 152 are hereinafter referred to as channels A, B, C and D and labeled accordingly in FIG. 8A.

Channels A, B and C are 5 mm long and the separation channel D has a length of 30 mm. The chip was isotropically etched to a depth of 45 μm, producing a channel with a semi-circular cross section and a width of 100 μm at the top. The cross sectional area of the channels is equivalent to that of a cylindrical capillary with an internal diameter of 70 μm. Other structures were fabricated to study the effect of channel folding, a common technique used to create compact structures in microfabricated devices. In these other structures, channels A, B and C are 5 mm long and the folded separation channels are 100 and 300 mm in length. The etch depth for the folded devices are 60 μm, resulting in 130 μm-wide channels. Two different intersection geometries were fabricated in the folded channel chips. In the first case all four channels meet at a single point, while in the other, channels A and C are offset vertically by 250 μm.

Coating. The inner channel surfaces of these microfabricated devices were coated using a modified Hjerten procedure. A filtered solution of 1.0 M NaOH was flushed through the channels for 10 min followed by a 12-hour etching period. The channels were subsequently rinsed with filtered deionized water, 0.1 M HCl, deionized water, and MeOH, 10 min each, and then dried in a stream of He 6.0 (Boc Group, Murray Hill, N.J.). The channels were then rinsed for 10 min with a filtered solution consisting of 5.0 mL 95% MeOH/water, 0.5 mL 10% HAc and 1.0 mL 3-(Trimethoxysilyl) propylmethacrylate (Fluka, Buchs, Switzerland). After 12 hours, the channels were rinsed first with MeOH then with deionized water, 10 min each. The channels were again dried with He 6.0. In the last step, 70 mg of acrylamide (Pharmacia, Uppsala, Sweden) dissolved in 1.0 ml of separation buffer (see below) and kept air-tight in a glass vial with septum was purged with He 6.0 at room temperature to remove any traces of oxygen. After 2 hours, 8 µL each of 100% TEMED (Sigma, St. Louis, Mo.) and of 20% APS (Pharmacia, Uppsala, Sweden) in water were added by a syringe to the acrylamide solution. After brief vortexing, the mixture was pulled up through the septum into a syringe and pressed into the etched channels. After 12 hours of polymerization at room temperature excess polymerized coating solution was purged from the channels using a syringe. The channels were then ready to be filled with the replaceable separation matrix.

Separation Matrix. The working buffer consisted of 1 X TBE with 3.5 M urea and 30% v/v formamide (Pharmacia, Uppsala, Sweden). A solution of 4% acrylamide w/v in working buffer kept in a glass vial equipped with a septum, was purged with He 6.0. After 2 hours two mL each of 10% TEMED and 10% APS (both in water) were added with a syringe through the septum. The mixture was briefly vortexed and allowed to polymerize for 12 hours. Aliquots of the matrix (stored at 4° C.) were transferred into a syringe and pushed into the coated microchip channels. This operation was performed with the aid of a mechanical fixture and could be fully automated in future generations of the apparatus.

Robotic Sample Preparation. A robotic system was used to prepare the STR samples. This consisted of T265 robotic arm on a linear track (CRS Robotics, Burlington, OT, Canada), a microplate feeding station (Eastern Technical Sales, Manchester, N.H.), a liquid pipetting station (Rosys, Wilmington, Del.), a heat block, and Progene thermal cyclers (Techne, Princeton, N.J.). Bloodstain card punches in 96-well Cycleplates (Robbins Scientific, Sunnyvale, Calif.) were washed with FTA Purification Reagent (Fitzco, Minneapolis, Minn.), TE (1 mM Tris-HCL, 0.5 mM EDTA, pH 8.0), and ethanol. A volume of 30 mL of PCR mix [1×STR buffer (Promega, Madison, Wis.), 5'-fluorescein labeled CTTv Quadruplex primer pairs (5 mM of each primer) (Promega), bovine serum albumin (60 mg/mL) and Amplitaq Gold DNA polymerase (50 mg/mL) (Applied Biosystems Division-Perkin Elmer, Foster City, Calif.)] was added to each well, followed by 25 mL of liquid wax (MJ Research, Watertown, Mass.). Thermal cycling was attained at 95° C. for 10 min, 10 cycles of 94° C. for 1 min, 60° C. for 1 min, and 70° C. for 1.5 min, 20 cycles of 90° C. for 1 min, 60° C. for 1 min, and 70° C. for 1 min, and 70° C. for 10 minutes.

Instrumentation. A schematic of the microchip genotyping apparatus is shown in FIG. 7. In brief, a fused silica microchip was mounted on a temperature-controlled stage with high voltage connections and optical access for laser induced fluorescence (LIF) detection. The microchip was affixed to an $Al_2O_3$ alumina heater block whose temperature was controlled by a temperature controller (Omega Instruments,Stamford, Conn.) and a series of thermocouples. The alumina block contained a machined aperture to allow for optical access of the detection zone.

High voltage was provided to platinum wire electrodes mounted in the four glass fluid reservoirs by a SL150 power supply (Spellman, Plainview, N.Y.). The voltages applied to each reservoir were controlled by a manual switching circuit and a resistor-based voltage divider network. Laser-induced fluorescence detection was achieved using an Innova 90 argon ion laser (Coherent, Santa Clara, Calif.) operating all lines. The beam was focused to a spot size of 15 µm in the channel at 30° C. angle of incidence with a 10 cm focal length lens. A 50X, 0.45 N.A. long working distance microscope objective (Bausch & Lomb, Rochester, N.Y.) collected the fluorescence emission. The collected light was spatially filtered by a 4-mm-diameter aperture in the image plane and optically filtered by two 520DF20 bandpass filters (Omega Optical, Brattleboro, Vt.) and detected by a photomultiplier detection system. The PMT current signal was converted to voltage across a 100 k_resistor, digitized with a PC-controlled 20-bit data acquisition system (Data Translation, Marlborough, Mass.), and analyzed using C Grams software (Galactic Industries, Salem, N.H.).

Microchip Separations. For fast genotyping, all four channels of the chip described in FIG. 8A were filled with the polyacrylamide separation matrix through a syringe interfaced to the separation channel exit hole. The detector was placed 26 mm from the injector. The freshly filled chip was pre-electrophoresed for 3 min at 200 V/cm across the separation channel at 50° C. To separate the CTTv internal standard ladder, 2 µL of the ladder was diluted with 8 µL working buffer. For the allelic profiling, 4 µL of PCR amplified sample was added to 2 µL of CTTv ladder and diluted to a total volume of 10 µL with 2×TBE buffer (3.5 M urea, 30% v/v formamide). The samples were briefly vortexed, denatured for 2 min at 95° C., chilled on ice and pipetted into the microchip sample vial located at the end of channel A. The chip was operated in the pinched cross injection mode, in which three ionic currents are merged at the injection point to confine the sample ions to the volume defined by the channel intersection. To load the sample, 400 V/cm was applied across channels A and C. Field strengths of 40 V/cm were applied to channels B and D to prevent the sample from entering these channels. This resulted in a stable injection plug length of 100 µm and an injection volume of approximately 0.36 nL. To inject the representative sample plug into the separation channel, the voltages were switched to create a field strength of 200 V/cm in the separation channel, and approximately 20 V/cm in the channels A and C. This generated a well defined plug entering the separation channel D with no excess leakage of sample from the side channels A and C. For experiments at higher field strengths, all voltages were equally multiplied. Similar field strengths were used in the 100 mm and 300 mm folded channel microchip devices resulting in injection plug lengths of 130 µm and 250 µm respectively, depending on the intersection geometry. Samples were changed by rinsing the sample reservoir A three times with separation buffer, loading the new sample, and pre-electrophoresis for several seconds through the cross channel to prevent sample carry-over.

Slab Gel Electrophoresis. Three microliters of 5'-fluorescein labeled CTTv ladder (diluted 1:5) was mixed with 3 µL of formamide containing 5'-Rox labeled Genescan-2500 size standard (Applied Biosystems Division Perkin Elmer, Foster City, Calif.). The sample was maintained at 95° C. for 2 min, quickly cooled in ice, and electrophoresed for 2.5 hours at 28 W through a denaturing 8% polyacrylamide gel in Applied Biosystems 373 DNA sequencer running Genescan software. The sizes of the CTTv ladder and PCR products were automatically determined by Genescan analysis software using the local Southern method. The polyacrylamide gel was pre-run for 20 min before loading the samples.

Example 1

Determination of Factors which Influence the Speed of STR Analysis

Figure 12A:
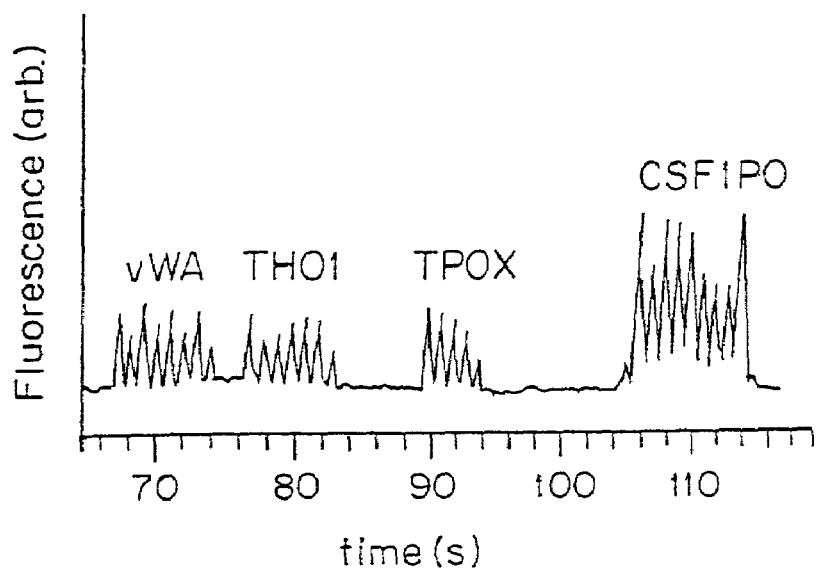
FIG. 12A is a microchip electropherogram for the four loci CTTv allelic sizing standard.

Initially, the general operation of the microfabricated device for genotyping by STR analysis was characterized. The objective was to determine the factors which influence the ultimate speed of such analyzes in microchip devices. Device performance was followed for the STR system CTTv, which consists of the four loci CSF1PO, TPOX, THO1 and vWA, each of which contains STR alleles which differ in length by four base pairs. The four loci, CSF1PO, TPOX, THO1 and vWA, contain 9, 5, 7, and 8 common alleles respectively. FIG. 12A shows the separation of the CTTv ladder ranging from 140 to 330 bases by microchip gel electrophoresis using one of our devices. This ladder was used as an internal sizing standard for the allelic profiling. In FIG. 12A the alleles of all the four loci are well resolved in less than two minutes with measured resolution R, $$R = ([2\ln 2]^{1/2})(t_2 - t_1)/(hw_1 + hw_2) \qquad (1)$$

where $t_n$ is the retention time of the $n^{th}$ peak and $hw_n$ is the full width at half-maximum of the $n^{th}$ peak. The resolution ranges from 1.7 for the vWA locus to 1.1 for the CSF1PO locus. We chose a minimum resolution of R=1.0, which is typically required for forensic applications, as a requirement while we optimized for analysis speed. This level of resolution is easily achieved in our microchip in a separation time that is approximately two orders of magnitude faster than conventional slab gel electrophoresis.

The interdependent parameters varied were operating temperature, channel shape (straight or serpentine), field strength, injection plug length, and channel length. Injection plug length was varied from 100 µm to 250 µm using simple cross and offset cross injectors. Channel length was varied between 13 mm and 295 mm.

After initial experiments at room temperature, the device was operated at 5° C. throughout the optimization process. Heating of the matrix assisted in keeping the samples denatured, and resulted in a nearly two-fold decrease in analysis time when compared to ambient temperature, this decrease is attributed to a decrease in the viscosity of the sieving gel. There were no observed changes in selectivity or peak width relative to operation at room temperature. Temperatures above 50° C. were found to be impractical, primarily due to bubble formation in the channels.

For STR analysis, serpentine channel bends were found to significantly degrade device performance. A band-broadening effect was observed which can be quantitatively explained by a simple geometrical calculation of the path length differences introduced by the turns, under the assumption that cross-channel migration randomizes molecular paths completely between turns. In contrast, analysis of data from straight channel devices revealed that these separations were essentially injection-plug limited. The absence of other measurable band broadening effects underlines the near ideal performance of our microchip gel system.

Figure 13:
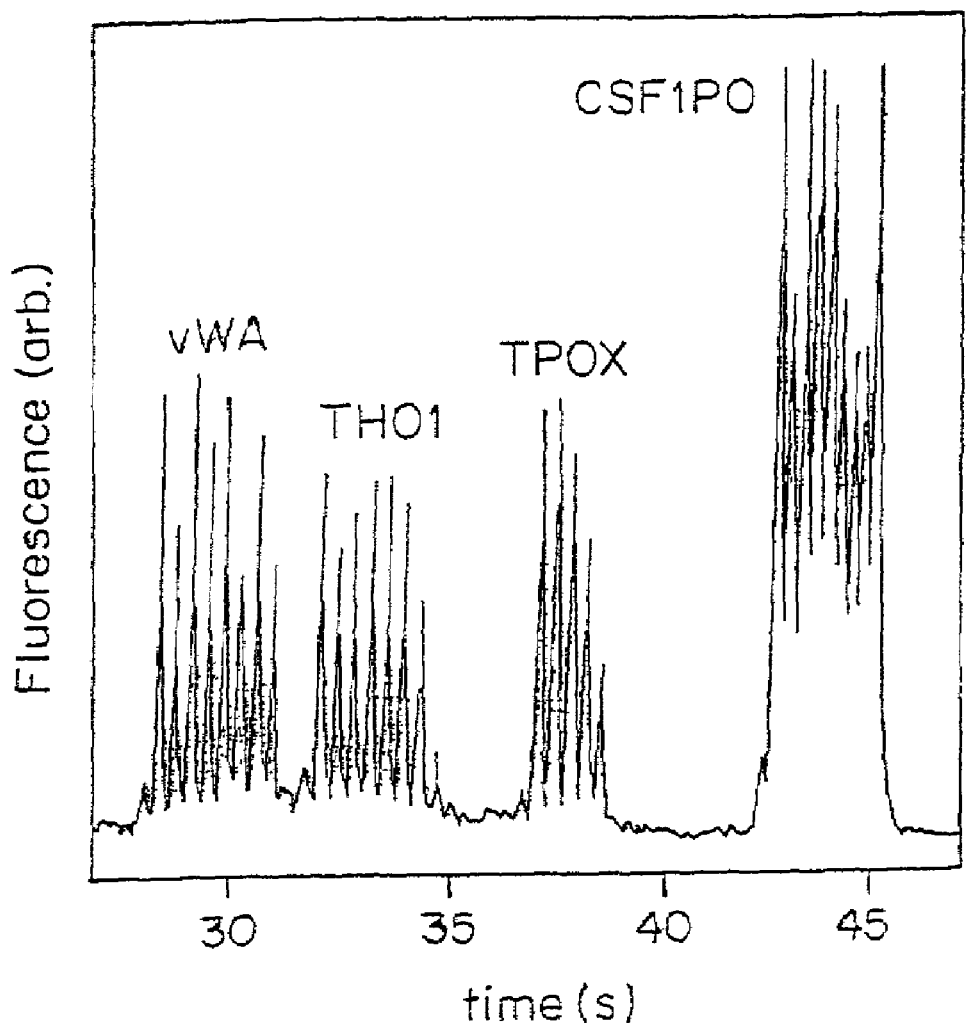
FIG. 13 is another microchip electropherogram for the four loci CTTv allelic sizing standard.

The field strength determines the migration speed within the device and influences the performance of the sieving matrix. Experimentally, the field strength was increased from values typical for capillary gel electrophoresis (approximately 200 V/cm) to values as high as 800 V/cm. At high fields, the resolution suffered due to the onset of new molecular sieving mechanisms such as biased reptation. The highest field at which a resolution of R=1 was maintained depended on the specific locus. As an example, FIG. 13 displays results of a separation at 500 V/cm where the vWA locus is baseline separated in thirty seconds. At a field strength of 800 V/cm the device performance became unpredictable and required replacement of the polyacrylamide solution to recover performance. Below 600 V/cm the device and sieving matrix exhibited excellent long term stability. An increase in migration times of about 10% was found during the course of 10 consecutive runs. However, the original migration times could be restored by replacing the gel-buffer system. In addition, the accuracy of the allele assignment was not affected by small changes in migration time since an internal standard was used for allele identification. No other changes in separation were observed even after 20 consecutive runs without replacement of the gel-buffer system. Occasionally a high fluorescence background was seen which was most likely due to contamination of the injection or detection zones with dust particles. Replacement of the gel-buffer system consistently restored the background signal to normal. A single microchip device was used for allelic profiling for an entire week (about 20 to 30 separations per day) at 50° C. with no noticeable deterioration. The polyacrylamide matrix was routinely replaced every morning after it was found that overnight storage of the chip at 4° C. could lead to a decrease in performance. The wall coating showed no degradation during continuous use over the course of one week.

The channel length required for a minimum resolution of R=1 depended primarily on field strength and injector length. The different injectors were characterized by varying field strength and effective channel length (the latter by moving the position of the detector along the length of the microfabricated channel). Minimum channel length with a given injector and given field is set by the acceptable resolution for the locus of interest.

Example 2

Assay of PCR Amplified Samples

Figure 12B:
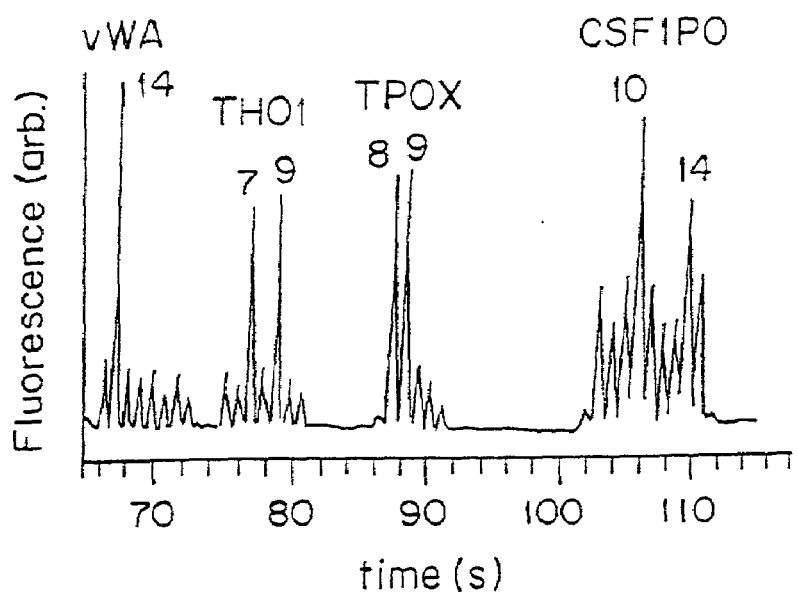
FIG. 12B is a microchip electropherogram presenting the allelic profile of an individual obtained by spiking a PCR amplified sample with the CTTv sizing standard.

The microchip device was used for genotyping of PCR amplified samples of eight individuals which were spiked with the CTTv ladder as the internal size standard and assayed on the microchip gel system. In all eight cases, the alleles could be identified with no ambiguity in under two minutes and the results were in complete agreement with data produced by traditional slab gel electrophoresis, which typically required 80, 94, 112 and 143 min to detect and resolve the alleles of vWA, THO1, TPOX, and CSF1PO respectively. The spiking experiment for one of the individuals is shown in FIG. 12B. The individual is clearly homozygous for vWA (allele 14) and heterozygous for THO1 (alleles 7/9), TPOX (alleles 8/9) and CSF1PO (alleles 10/14).

Results, thus, have demonstrated that the quadrupled STR system CTTv can be analyzed with high accuracy in less than two minutes and a single locus in 30 seconds by microchip gel electrophoresis. Compared to capillary or slab gel electrophoresis, the approach described herein device is faster by a factor of ten or one-hundred, respectively. In addition, the present system can be operated for an extended period of time in a highly reliable manner.

The high speed of analysis can be explained by the fact that microchips allow very short and precisely controlled injection plug widths (100 µm and less). These narrow injections permit short separation distances and consequently shorter analysis times and result in reduced diffusion. The influence of a given injection plug length on total analysis time can be estimated according to Eq. 2

$$R_t = 0.25 D_\mu t E (s_1^2 + 2Dt)^{-1/2} \qquad (2)$$

where the theoretical resolution $R_t$ is calculated under the assumption that injection and diffusion are the sole contributors to peak width. In this expression, $D\mu$ is the difference of mobility of two neighboring DNA fragments, E is the electric field strength, t is the fragment migration time, $s_1^2$ is the variance due to injection broadening, and 2Dt is the variance of the diffusion contribution with the diffusion coefficient D. Other effects, such as broadening due to detection or thermal gradients across the channel were not observed in our system. Optimal performance was only obtained when straight separation channels were used, since in folded channels, as discussed previously, the broadening effect of the channel bends dominated.

Figure 14:
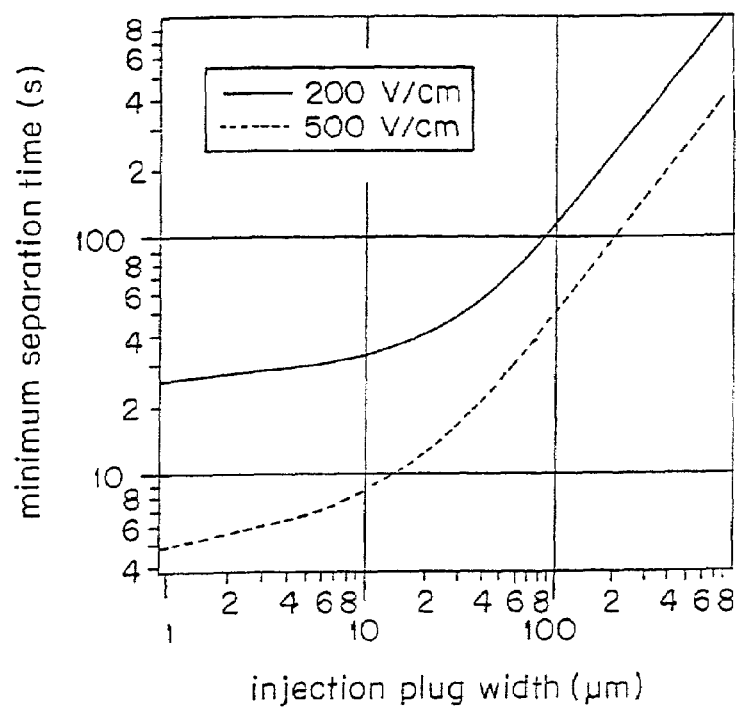
FIG. 14 is a graphic representation of predicted minimum separation time required to achieve a resolution of 1.0 for the last two alleles of the CSF1PO locus as a function of the injection plug width at 200 and 500 V/cm in the presence of a 4% linear polyacrylamide (1×TBE buffer with 3.5 M urea and 30% v/v formamide) sieving matrix at 50° C.

FIG. 14 shows the calculated separation times required to achieve a resolution of $R_t=1$ for the last pair of alleles in the CSF1P0 locus as a function of injection width at two different field strengths. Since this locus is always the most difficult to separate it determines the overall CTTv analysis time for the full quadruplex system. These calculations are based on electrophoretic mobilities and diffusion coefficients determined experimentally for the CTTv ladder in our microchip gel system. Two extremes can be distinguished for the separation at 200 V/cm. In the case where the injection plug is larger than 100 mm, the minimum separation time is linearly dependent on plug width and independent of diffusion. Below 10 mm injection width the situation is reversed; the system becomes diffusion limited and almost independent of injection width. Any further decrease in injection plug length will therefore not result in a significant decrease in minimum separation time. The theoretical time in the limit of zero injection width is predicted by Eq. (2) with $s_I=0$. In this limit, resolution is determined by parameters which are solely gel dependent. A minimum separation time of 26 seconds for the CTTv system, corresponding to a separation distance of 6 mm, was calculated for 200 V/cm. This is only a factor of 4 faster than what was obtained in this study where we have been restricted by available devices to a minimum injection width of 100 $\mu$m. The predicted result would require a 10 $\mu$m injector, which in our system would not be feasible without an improved detector, or a pre-concentration step of the STR samples. However, we consider an injection plug length between 25 $\mu$m and 50 $\mu$m as being practical for routine STR analysis with our system. The curve for the separations at 500 V/cm shows a similar behavior with even greater improvement predicted for scaled down injectors. A device utilizing injectors between 25 $\mu$m and 50 $\mu$m with a separation length of 14 mm at 500 V/cm should result in a total separation time of 15 to 25 seconds for the full CTTv ladder. Despite the observed loss in selectivity at 500 V/cm primarily due to biased reptation, adequate resolution is maintained because of the decreased diffusional broadening due to short analysis times with the higher field.

Figure 15:
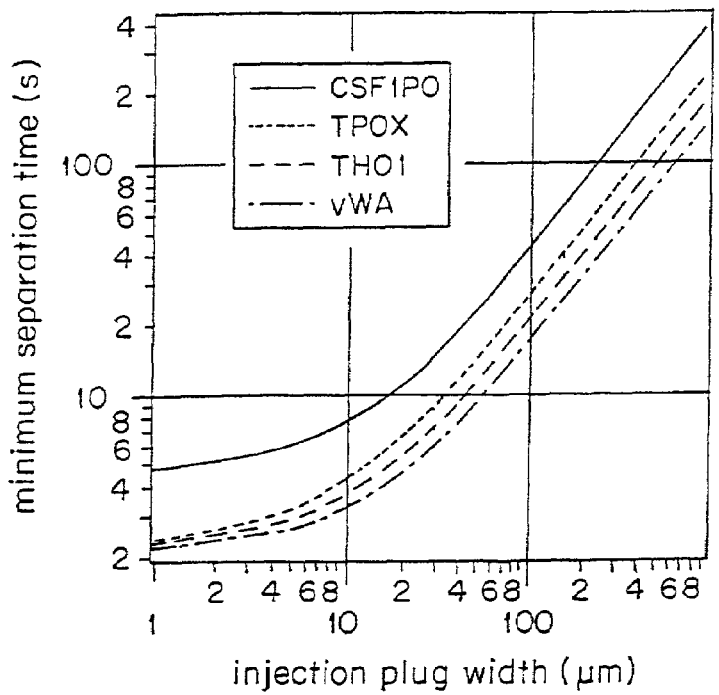
FIG. 15 is a graphic representation of predicted minimum separation time required to achieve a resolution of 1.0 for the last two alleles of each locus of the CTTv system as a function of the injection plug width at 500 V/cm in the presence of a 4% linear polyacrylamide (1×TBE buffer with 3.5 M urea and 30% v/v formamide) sieving matrix at 50° C.

FIG. 15 shows the same analysis at a field strength of 500 V/cm for each of the four loci of the CTTv analysis. As above, the calculations are based on electrophoretic mobilities and diffusion coefficients measured for the CTTv ladder in our microchip gel system. The first three loci show very similar behavior. Extremely high speed analysis should be possible for these lower molecular weight fragments. It should be possible to perform STR analysis of the first three loci using a 25 $\mu$m injector in less than 4 seconds.

Thus genotyping for a single locus has been performed in 30 seconds and the CTTv STR system consisting of four loci has been analyzed reliably in less than two minutes in a microchip system. The device is already highly optimized and can perform repeated analyses without replacement of the sieving matrix. Further optimization will occur with an improved fabrication geometry which would allow injection plugs between 25 $\mu$m and 50 $\mu$m in length. The current device uses sample volumes of 4 $\mu$L from standard PCR preparations, although the use of even smaller volumes should be possible without loss in performance. The current microchip system offers an improvement in speed over current technology of almost two orders of magnitude, with no compromise in quality for standard quadruplex CTTv analyses.

Example 3

Evaluation of the Feasibility of Loading Schemes

A glass microchip with laser-drilled injection ports leading to microchannels was interfaced with a 1 cm thick gasket fabricated from polydimethylsiloxane (PDMS) silicone elastomer material (Dow Coming Sylgard 184, Schenectady, N.Y.). Capillaries of inner diameter 100 $\mu$m and outer diameter 375 $\mu$m were molded into the gasket and set in place while the PDMS cured to a semi-rigid final state. No rigid support structure was used in these trials, and the capillary-gasket system was aligned to the injection holes on the microchip manually with the aid of a microscope. The free end of the 10 cm long capillary was inserted into a container of fluorescein and a voltage of 50 volts per centimeter was applied between the container and the microchip channels. The microchip was illuminated with an argon ion laser source operating at 488 nm, and the fluorescing fluorescein was observed flowing from its original container to the microchannels via the elastomer gasket with no leakage at the interface between the gasket and the quartz microchip.

The elastomer gasket, with the capillary molded into it, was subsequently removed from the microchip, cleaned by rinsing with a stream of water, dried, and then replaced on the microchip. The experiment was repeated successfully over ten times, after which the interfacial surface of the elastomer gasket became sufficiently contaminated with dirt, primarily due to handling, that a hermetic seal was no longer able to be achieved.

While this invention has been particularly shown and described with references to preferred embodiments thereof, it will be understood by those skilled in the art that various changes in form and details may be made therein without departing from the scope of the invention encompassed by the appended claims.

What is claimed is:

1. A test module assembly, comprising:
   a dielectric plate member having an upper planar surface and a lower planar surface that is spaced apart from and parallel with the upper planar surface, the dielectric plate member having at least one set of channels that includes an injection channel and a separation channel, the injection channel having an end at the upper planar surface and another end at the lower planar surface, each end of the injection channel configured to allow fluid to penetrate the respective planar surface, the separation channel extending within the dielectric plate member in a plane parallel with the upper and lower planar surfaces and intersecting the injection channel, the separation channel having ends, each end not coincidental with an intersection between the injection channel and the separation channel; and a housing that attaches to the dielectric plate member, the housing providing (i) a first opening over the upper planar surface such that a first end of the injection channel is accessible through the first opening, and (ii) a second opening over the lower planar surface such that a second end of the injection channel is accessible through the second opening.

2. The test module assembly of claim 1 wherein the injection channel intersects the separation channel at a right angle.

3. The test module assembly of claim 2 wherein the injection channel terminates at the upper and lower planar surfaces at right angles to the upper and lower planar surfaces.

4. The test module assembly of claim 1 wherein the injection channel terminates at the upper and lower planar surfaces at right angles to the upper and lower planar surfaces.

5. The test module assembly of claim 1 wherein the dielectric plate member is wedge shaped.

6. The test module assembly of claim 1 wherein the housing further provides a third opening over the upper planar surface such that the separation channel is accessible to a detection device through the third opening.

7. The test module assembly of claim 1 further comprising:

a heating device, supported by the housing, that provides heat to the dielectric plate member when power is provided to the heating device.

8. The test module assembly of claim 1 further comprising:

a first porous membrane that covers the first end of the injection channel and a second porous membrane that covers the second end of the injection channel to retain a matrix within the injection and separation channels, the first and second porous membranes being adhered to the dielectric plate member.

9. The test module assembly of claim 1 further comprising:

an electromagnetic unloading device, coupled to the housing, that draws magnetic material towards the dielectric plate member when the electromagnetic unloading device is activated.

10. The test module assembly of claim 1 wherein the dielectric plate member includes multiple sets of channels, each set of channels including an injection channel and a separation channel, the injection channel of each set extending from the upper planar surface to the lower planar surface, the separation channel of each set extending within the dielectric plate member in a plane parallel with the upper and lower planar surfaces and intersecting the injection channel of that set.

11. The test module assembly of claim 10 wherein the injection channels of the multiple sets of channels are parallel with each other.

12. The test module assembly of claim 1 wherein the dielectric plate member is rotatable, the rotatable dielectric plate member having multiple separation channels that extend within the rotatable dielectric plate member in a plane parallel with the upper and lower planar surfaces, the multiple separation channels extending radially from an inner portion of the rotatable dielectric plate member to an outer portion of the rotatable dielectric plate member.

13. The test module assembly of claim 12 wherein the rotatable dielectric plate member is disk shaped and further includes multiple injection channels, each of the multiple injection channels intersecting a corresponding one of the multiple separation channels within the outer portion of the rotatable dielectric plate member.

14. A test module assembly, comprising:

a dielectric plate member having an upper planar surface and a lower planar surface that is spaced apart from and parallel with the upper planar surface, the dielectric plate member having at least one set of channels that includes an injection channel and a separation channel, the injection channel extending from the upper planar surface to the lower planar surface, the separation channel extending within the dielectric plate member in a plane parallel with the upper and lower planar surfaces and intersecting the injection channel, the injection channel having a first and second end configured to allow fluid flow through the upper and lower planar surface respectively;

a first porous material that covers the first end of the injection channel and a second porous material that covers the second end of the injection channel to retain a matrix within the injection and separation channels; and a housing that attaches to the dielectric plate member, the housing providing (i) a first opening over the upper planar surface such that a first end of the injection channel is accessible through the first opening, and (ii) a second opening over the lower planar surface such that a second end of the injection channel is accessible through the second opening.

15. A test module assembly, comprising:

a dielectric plate member having an upper planar surface and a lower planar surface that is spaced apart from and parallel with the upper planar surface, the dielectric plate member having at least one set of channels that includes an injection channel and a separation channel, the injection channel extending from the upper planar surface to the lower planar surface, the separation channel extending within the dielectric plate member in a plane parallel with the upper and lower planar surfaces and intersecting the injection channel, the injection channel having a first and second end configured to allow fluid flow through the upper and lower planar surface respectively;

an electromagnetic unloading device positioned below the first end of the injection channel that draws magnetic material towards the dielectric plate member when the electromagnetic unloading device is activated; and a housing that attaches to the dielectric plate member, the housing providing (i) a first opening over the upper planar surface such that a first end of the injection channel is accessible through the first opening, and (ii) a second opening over the lower planar surface such that a second end of the injection channel is accessible through the second opening.

16. A test module assembly, comprising:

a dielectric plate member having an upper planar surface and a lower planar surface that is spaced apart from and parallel with the upper planar surface, the dielectric plate member having at least one set of channels that includes an injection channel and a separation channel, the injection channel extending from the upper planar surface to the lower planar surface, the separation channel extending within the dielectric plate member in a plane parallel with the upper and lower planar surfaces and intersecting the injection channel, the injection channel having a first and second end configured to allow fluid flow through the upper and lower planar surface respectively, the injection channel and the separation channel each substantially filled with a separation matrix for separating a biomolecular analyte; and a housing that attaches to the dielectric plate member, the housing providing (i) a first opening over the upper planar surface such that a first end of the injection channel is accessible through the first opening, and (ii) a second opening over the lower planar surface such that a second end of the injection channel is accessible through the second opening.

17. A test module assembly, comprising:

a dielectric plate member having an upper planar surface and a lower planar surface that is spaced apart from and parallel with the upper planar surface, the dielectric plate member having at least one set of channels that includes an injection channel and a separation channel, the injection channel extending from the upper planar surface to the lower planar surface, the separation channel extending within the dielectric plate member in a plane parallel with the upper and lower planar surfaces and intersecting the injection channel, the injection channel having a first and second end configured to allow fluid flow through the upper and lower planar surface respectively;

an electrode proximate with each of the at least two ends of the injection channel for promoting electrokinetics in the set of channels; and a housing that attaches to the dielectric plate member, the housing providing (i) a first opening over the upper planar surface such that a first end of the injection channel is accessible through the first opening, and (ii) a second opening over the lower planar surface such that a second end of the injection channel is accessible through the second opening.

18. A method for separating a sample of biomolecular analyte, comprising the steps of:

providing a test plate with a plurality of channels including injection channels and separation channels, the test plate oriented with each injection channel having a first end intersecting an upper surface of the test plate and a second end intersecting a lower surface of the test plate, each end of each injection channel configured to allow fluid to penetrate the respective surface, a portion of each separation channel being between the upper surface and lower surface of the test plate, the portion of each separation channel intersecting a respective injection channel, each separation channel having ends, each separation channel end not coincidental with an intersection between the respective injection channel and the separation channel;

providing a housing attached to the test plate having openings over the upper and lower surfaces of the test plate such that each end of each injection channel is accessible through a corresponding opening;

drawing the sample along one of the injection channels of the test plate using electrokinetics; and subsequently drawing the sample along the portion of the respective separation channel of the test plate using electrokinetics.

19. The method of claim 18 further comprising the steps of:

drawing multiple samples along multiple injection channels of the test plate using electrokinetics simultaneously with the step of drawing the sample; and drawing the multiple samples along portions of multiple separation channels of the test plate using electrokinetics, the portions of the multiple separation channels respectively intersecting the multiple injection channels.

20. The method of claim 19 further comprising the step of:

scanning the separation channel and the multiple separation channels with a detection device.

* * * * *